US009194008B2

(12) United States Patent
Gordon et al.

(10) Patent No.: US 9,194,008 B2
(45) Date of Patent: Nov. 24, 2015

(54) HYBRIDIZATION ASSAY DETECTION PROBES FOR DETECTING HUMAN PAPILLOMA VIRUS IN A SAMPLE

(71) Applicant: Gen-Probe Incorporated, San Diego, CA (US)

(72) Inventors: Patricia Gordon, Spring Valley, CA (US); Nick M. Carter, Galt, CA (US); Steven T. Brentano, Santee, CA (US); Philip W. Hammond, Ayer, MA (US)

(73) Assignee: Gen-Probe Incorporated, San Diego, CA (US)

( * ) Notice: Subject to any disclaimer, the term of this patent is extended or adjusted under 35 U.S.C. 154(b) by 155 days.

(21) Appl. No.: 13/924,087

(22) Filed: Jun. 21, 2013

(65) Prior Publication Data
US 2015/0037785 A1 Feb. 5, 2015

Related U.S. Application Data

(60) Continuation of application No. 12/965,728, filed on Dec. 10, 2010, now Pat. No. 8,501,410, which is a division of application No. 11/929,753, filed on Oct. 30, 2007, now Pat. No. 7,875,441, which is a continuation of application No. 10/601,913, filed on Jun. 23, 2003, now Pat. No. 7,470,512, which is a continuation of application No. 08/749,955, filed on Nov. 14, 1996, now Pat. No. 6,583,278.

(60) Provisional application No. 60/006,854, filed on Nov. 15, 1995.

(51) Int. Cl.
*C12Q 1/68* (2006.01)
*C12P 19/34* (2006.01)
*C12Q 1/70* (2006.01)

(52) U.S. Cl.
CPC .............. *C12Q 1/708* (2013.01); *C12Q 1/6886* (2013.01); *C12Q 1/6865* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,886,741 A | 12/1989 | Schwartz |
| 4,983,728 A | 1/1991 | Herzog et al. |
| 5,030,557 A | 7/1991 | Hogan et al. |
| 5,182,377 A | 1/1993 | Manos et al. |
| 5,185,439 A | 2/1993 | Arnold et al. |
| 5,283,171 A | 2/1994 | Manos et al. |
| 5,399,491 A | 3/1995 | Kacian et al. |
| 5,427,930 A | 6/1995 | Birkenmeyer et al. |
| 5,447,839 A | 9/1995 | Manos et al. |
| 5,484,699 A | 1/1996 | Bouma et al. |
| 5,527,898 A | 6/1996 | Bauer et al. |
| 5,580,970 A | 12/1996 | Hendricks et al. |
| 5,679,509 A | 10/1997 | Wheeler et al. |
| 6,214,544 B1 | 4/2001 | Fisher |

FOREIGN PATENT DOCUMENTS

| | | |
|---|---|---|
| DE | 4431174 A1 | 3/1996 |
| EP | 0313219 A2 | 4/1989 |
| EP | 0373352 A2 | 11/1989 |
| EP | 0402132 A2 | 12/1990 |
| EP | 0524807 A1 | 1/1992 |
| EP | 0477972 A2 | 4/1992 |
| EP | 0489442 A1 | 6/1992 |
| EP | 0524807 A1 | 1/1993 |
| EP | 0630973 A2 | 12/1994 |
| EP | 0671473 A1 | 9/1995 |
| FR | 2679254 A1 | 1/1993 |
| JP | 5-192200 | 8/1993 |
| WO | 88/03957 A1 | 6/1988 |
| WO | 88/06634 A1 | 9/1988 |
| WO | 89/02934 A1 | 4/1989 |
| WO | 89/09940 A1 | 10/1989 |
| WO | 90/02821 A1 | 3/1990 |
| WO | 91/08312 A1 | 6/1991 |
| WO | 91/10675 A1 | 7/1991 |
| WO | 94/26934 A2 | 11/1994 |
| WO | 95/28942 A1 | 11/1995 |
| WO | 96/06950 A1 | 3/1996 |

OTHER PUBLICATIONS

Jacobs et al, "Group-specific differentiation between high and low risk human papillomavirus genotypes by general primer-mediated PCR and two cocktails of oligonucleotide probes", J. Clin. Microbiol. 33(4):901-905, Apr. 1995.

Yamada et al, "Human papillomavirus type 16 variant lineages in United States populations characterized by nucleotide sequence analysis of the E6, L2 and L1 coding segments", J. Virol. 69(12):7743-7753, Dec. 1995.

Cossman et al., "Ch. 19—Detection of Human Papillomavirus Infection," in Molecular Genetics in Cancer Diagnosis, Elsevier, New York, pp. 331-348 (1990).

Evander et al., "Oligonucleotide primers for DNA amplifications of the early regions 1, 6, and 7 from human papillomavirus types 6, 11, 16, 18, 31, and 33," Arch. Virol. 116:221-233 (1991).

Gravitt and Manos, "Polymerase chain reaction-based methods for the detection of human papillomavirus DNA," in The Epidemiology of Cervical Cancer and Human Papillomavirus, edited by Munoz et al., International Agency for Research on Cancer, pp. 121-133 (1992).

Nagai et al., "Detection of Papillomavirus Nucleic Acids in Genital Precancers with the In Situ Hybridization Technique," International J. Gynecological Pathology 6(4):366-379 (1987).

(Continued)

*Primary Examiner* — Young J Kim
(74) *Attorney, Agent, or Firm* — Jeffrey E. Landes

(57) ABSTRACT

Hybridization assay detection probes targeted to HPV Type 16 nucleic acid sequences which are particularly useful to aid in detecting HPV type 16 are described. The oligonucleotides can aid in detecting HPV Type 16 by acting singly or as part of a detection probe mixture. Compositions, reaction mixtures and methods of use are provided.

12 Claims, 2 Drawing Sheets

(56) References Cited

OTHER PUBLICATIONS

Nielsen, "Human Papillomavirus Type 16/18 in Uterine Cervical Adenocarcinoma In Situ and Adenocarcinoma," Cancer 65(11):2588-2593 (1990).
Nishikawa et al., "Relatively Low Prevalence of Human Papillomavirus 16, 18 and 33 DNA in the Normal Cervices of Japanese Women Shown by Polymerase Chain Reaction," Jpn. J. Cancer Res. 82:532-538 (1991).
Resnick et al., "Detection and Typing of Human Papillomavirus in Archival Cervical Cancer Specimens by DNA Amplification with Consensus Primers," J. of National Cancer Institute 82(18):1477-1484 (1990).
Ritter et al., "Detection of human papillomavirus deoxyribonucleic acid in exfoliated cervicovaginal cells as a predictor of cervical neoplasia in a high-risk population," Am. J. Obstetrics & Gynecology 159(6):1517-1525 (1988).
Rodu et al., "Simplified PCR-Based Detection and Typing Strategy for Human Papillomavirus Utilizing a Single Oligonucleotide Primer Set," BioTechniques 10(5):632-636 (1991).
Sambrook et al., Molecular Cloning: A Laboratory Manual 2:11 (2d ed. 1989).
Schneider et al., "Papillomavirus Infection of the Lower Genital Tract: Detection of Viral DNA in Gynecological Swabs," Int. J. Cancer 35:443-448 (1985).
Schneider-Gadicke and Schwarz., "Different human cervical carcinoma cell lines show similar transcription patterns of human papillomavirus type 18 early genes," The EMBO J 5(9):2285-2292 (1986).
Seedorf et al., "Identification of early proteins of the human papilloma virus type 16 (HPV 16) and type 18 (HPV 18) in cervical carcinoma cells," The EMBO J. 6(1):139-144 (1987).
Smotkin et al., "Oncogenic and Nononcogenic Human Genital Papillomaviruses Generate the E7 mRNA by Different Mechanism," J. of Virology 63(3):1441-1447 (1989).
Stoler et al., "In Situ Hybridization Detection of Human Papillomavirus DNAs and Messenger RNAs in Genital Condylomas and a Cervical Carcinoma," Human Pathology 17(12):1250-1258 (1986).
Tsunokawa et al., "Presence of Human Papillomavirus Type-16 and Type-18 DNA Sequences and Their Expression in Cervical Cancers and Cell Lines from Japanese Patients," Int. J. Cancer 37:499-503 (1986).
Villa et al., "An approach to human papillomavirus identification using low stringency single specific primer PCR," Molecular and Cellular Probes 9:45-48 (1995).
Yokota et al., "Detection of Human Papillomavirus Types 6/11, 16 and 18 in Exfoliated Cells from the Uterine Cervices of Japanese Women with and without Lesions," Jpn. J. Cancer Res. 81:896-901 (1990).
Young et al., "PCR for the Detection of Genital Human Papillomavirus Infection: A Mixed Blessing," Ann. Med. 24:215-219 (1992).
Doeberitz et al., "Influence of chromosomal integration on glucocorticoid-regulated transcription of growth-stimulating papillomavirus genes E6 and E7 in cervical carcinoma cells," Medical Sciences 88:1411-1415 (1991).
Costa et al., "Is Vestibular Papillomatosis Associated With Human Papillomavirus?" J. of Medical Virology, 35:7-13 (1991).
Gius et al., "Inducible and Constitutive Enhancer Domains in the Noncoding Region of Human Papillomavirus Type 18," J. of Virology 62(3):665-672 (1988).
Inagaki et al., "Nucleotide Sequences of cDNAs for Human Papillomavirus Type 18 Transcripts in HeLa Cells," J. or Virology 62(5):1640-1646 (1988).
Lucotte et al., "A mulitple primer pairs polymerase chain reaction for the detection of human genital papillomarvirus types," Mol. Cell. Probes 7:339-344 (1993).
Van Ranst et al., "Phylogenetic classification of human papillomaviruses: correlation with clinical manifestations," J. Gen. Vir. 73:2653-2660 (1992).
Marshall et al., "Trans-Regulation and Differential Cell Specificity of Human Papillomavirus Types 16, 18, and 11 Cis-Acting Elements," J. Medical Virology 29:115-126 (1989).
Requisition by the Examiner, Canadian Patent Application No. 2,237,891, mailed May 3, 2012.

HYBRIDIZATION ASSAY DETECTION PROBES FOR DETECTING HUMAN PAPILLOMA VIRUS IN A SAMPLE

RELATED APPLICATIONS

This application is a continuation of U.S. Pat. No. 8,501,410, filed on Dec. 10, 2010, which is a divisional of U.S. Pat. No. 7,875,441, filed on Oct. 30, 2007, which is a continuation of U.S. Pat. No. 7,470,512, filed Jun. 23, 2003, which is a continuation of U.S. Pat. No. 6,583,278, filed Nov. 14, 1996, which claims the benefit under 35 U.S.C. §119(e) of U.S. provisional application no. 60/006,854, filed Nov. 15, 1995.

FIELD OF THE INVENTION

This invention relates generally to nucleic acid probes complementary to Human Papillomavirus (hereafter "HPV") nucleic acids, methods of using such probes, and kits containing such probes. In particular, different types of oligonucleotide probes are described (including hybridization assay probes, helper oligonucleotides and amplification oligonucleotides) which are useful for detecting HPV Type 16 and/or Type 18 in a test sample, such as a vaginal swab, a cervical swab, a urethral swab, a tissue sample, a body fluid or an experimental solution.

BACKGROUND OF THE INVENTION

The following description of the background of the invention and references cited therein are not admitted to be prior art to the present invention.

Papillomaviruses are small DNA viruses. These viruses are associated with and/or thought to be the causative agent of a range of benign conditions (including benign lesions and benign tumors). Papillomaviruses have also been associated with malignancies such as squamous cell carcinoma in patients having the autosomal disease epidermodysplasia verricruciformis, and with genital cancers in both males and females.

There have now been at least 59 different types of HPV characterized, (see Manual of Clinical Microbiology; 998-1000; 5th ed. American Soc. for Microbiol. 1991). The genome of different HPV variants appears to be similar between all types (Van Ranst et al., J. Gen. Vir., 73:2653-60, 1992). Nonetheless, HPVs have been subject to differential typing, based on differences in the DNA sequences of different strains of the virus (Id.).

Among those HPV types associated with genital cancers are HPV types 16, 18, 31, 33 and 35. These five strains collectively are found in over 80% of all cervical tumors, suggesting a causative role.

Antigen detection of HPV types 16 and 18 has been described, but it is reported that commercially available sera react with antigens shared by all papillomaviruses (Roman and Fife, Clin. Microbiol. Rev. 2:166-190, 1989). In addition, the percentage of antigen-positive specimens is reported to decrease as the severity of the disease increases from mild dysplasia to carcinoma in situ, to invasive carcinoma (Id.).

In vivo, HPV DNA is found both episomally and integrated in the host genome. The HPV genome contains open reading frames encoding from 8 to 10 proteins, although not all of these proteins have been identified. Many of these open reading frames have been designated with the prefixes E or L, referring to "early" or "late" transcription events, although not all of those designated "early" are actually transcribed early, and vice versa.

Descriptions of certain primers and oligonucleotide probes for the detection of the E6 region of HPV types 16 and 18 are provided in Lucotte et al., Mol. Cell. Probes 7:339-344, 1993; De Britton et al., Obst. Gynec. 81:19-24, 1993; Nuovo, et al., Am. J. Pathol. 138:53-58, 1991; Van der Velde et al., J. Med. Virol. 36:279-282, 1992; Thompson et al., J. Med. Virol. 36:54-6, 1992; Cornelissen et al., J. Gen. Virol. 71:1243-1246, 1990, Hus and McNicol, Mol. Cell. Probes 6:459-466, 1992; Sang and Barbosa, Virol. 189:448-455, 1992; Joseph, European Pub. No. 0 477 972; Joannes et al., PCT Pub. No. WO 93/02217; Emery et al., PCT Pub. No. WO 92/01815; Hendricks, PCT Pub. No. WO 91/08312, PCT Pub. No. PCT/US90/07057; Manos et al., U.S. Pat. No. 5,182,377; Herzog, et al., U.S. Pat. No. 4,983,728; Schwartz and Adams, PCT Pub. No. WO 89/02934; George and Groff, PCT Pub. No. WO 89/09940; Nur et al., PCT Pub. No. WO 92/14847; Mazzatente et al., European Pat. Pub. No. EPO 489 442; Shimada et al., European Pat. Pub. No. EPO 402 132; and Morris et al., PCT Pub. No. WO 88/06634; all of which are hereby incorporated herein by reference in their entirety (including drawings).

SUMMARY OF THE INVENTION

The present invention features oligonucleotides useful for detecting HPV Type 16 and/or Type 18, methods of making and using these oligonucleotides, and kits containing the oligonucleotides. The featured oligonucleotides include hybridization assay oligonucleotides, amplification oligonucleotides, and helper oligonucleotides. The different oligonucleotides can aid in the detection of HPV Type 16 and/or Type 18 in different ways.

Hybridization assay probe oligonucleotides are targeted to HPV Type 16 and/or Type 18 regions and preferably are labeled. These oligonucleotides are particularly useful for distinguishing between HPV Type 16 and/or Type 18 variants from other HPV variants, including HPV 6, 11, 31, 33, 35, 39, 45, 51, 52, or 58. The target region for the hybridization assay oligonucleotides includes nucleic acids specifically found in HPV Type 16 and/or Type 18, or a nucleic acid sequence complimentary thereto. Complimentary nucleic acid can be produced using standard well known nucleic acid amplification techniques.

The amplification primers can be used to initiate amplification reactions using HPV target nucleic acid. The primers are designed to hybridize to a region of the target nucleic acid 3' of a target region. The primers can be used to initiate amplification synthesizing copies of nucleic acid complementary to the target region. Different types of amplification can be performed depending upon the amplification primer which is utilized. For example, pairs of amplification primers hybridizing to a region 3' of the target sequence and to a region 3' of a complimentary target sequence can be used in PCR amplification. Primers which hybridize to a region 3' to the target sequence which have a promoter sequence recognized by a promoter (such as those used by bacteriophage T7, T3 or SP-6) can be used to synthesize multiple copies of nucleic acid complimentary to the target sequence.

Helper probes are particularly useful for facilitating the hybridization of a hybridization assay oligonucleotide to its target sequence. Helper probes aid in altering the secondary structure of nucleic acid in and around the target region. The use of helper probes is described by Hogan and Milliman, U.S. Pat. No. 5,030,557, which is incorporated by reference herein in its entirety including any drawings. Also featured are probe mixes containing one or more labeled probes and at least one helper probe for use in hybridization assays for the detection of HPV and methods of detecting and amplifying HPV nucleic acids.

The probes, their complements or RNA equivalents, can be used to distinguish HPV Type 16 and/or Type 18 from closely related phylogenetic neighbors, by preferentially hybridizing to an HPV Type 16 and/or Type 18 target nucleic acid sequence region under selective hybridization assay conditions. The hybridization assay probes disclosed herein are particularly useful for detecting the presence of HPV Type 16 and/or Type 18 and/or for determining the quantity of HPV Type 16 and/or Type 18 present in a test sample, e.g., samples of sputum, urine, blood, tissue sections, urogenital secretions, urogenital swabs and other clinical samples.

Hybridization assay oligonucleotide probes contain a nucleotide sequence perfectly complementary, or substantially complementary, to an HPV target sequence. In addition to having a region designed to distinguish between HPV Type 16 and/or Type 18 on the one hand and different HPV variants on the other hand, hybridization assay probes can also have one or more additional nucleic acid sequences which are complementary to additional stretches of an HPV target nucleic acid or non-complementary nucleic acid sequences. For example, the additional sequences can be complementary to both HPV Type 16 and/or Type 18 and other HPV variants, they can be non-complementary to HPV Type 16 and/or Type 18, or HPV variants, or they can even have a slightly higher degree of complementarity to the HPV variants as long as the hybridization probe is able to distinguish HPV Type 16 and/or Type 18 from other HPV variants such as HPV types 6, 11, 31, 33, 35, 39, 45, 51, 52, or 58.

Hybridization assay probes are sufficiently complementary to nucleic acids containing a target sequence to form a stable and detectable hybrid probe:target duplex under stringent hybridization assay conditions. A hybridization assay probe is preferably between 10 and 100 nucleotides in length, more preferably between 14 and 50 nucleotides in length. Even more preferably the probe is between 18 and 40 nucleotides in length. Hybridization assay probes are preferably labeled with a reporter group moiety such as a radioisotope, a fluorescent moiety, a chemiluminescent moiety, an enzyme, or a ligand incorporated into the probe. The moiety can be used to detect or confirm probe hybridization to its target sequence. A hybridization assay probe is an oligonucleotide which can distinguish HPV type 16 and/or 18 from other HPV types and or common body flora, by preferentially hybridizing to an HPV type 16 and/or 18 target nucleic acid sequence region under stringent hybridization assay conditions.

I. Hybridization Assay Probes

Thus, in one aspect the invention features a hybridization assay probe containing an oligonucleotide able to hybridize to an HPV Type 16 and/or Type 18 target nucleic acid to form a detectable target:probe duplex under selective stringency hybridization conditions, but which preferably will not form a detectable non-target:probe duplex with nucleic acids from HPV Types 6, 11, 31, 33, 35, 39, 45, 51, 52, and/or 58. The oligonucleotide comprises a sequence of nucleic acids which is at least 70%, (preferably 80%, more preferably 90%, and most preferably 100% complementary) to a target sequence of 10 or more contiguous nucleotides present in a target region. The target regions can be better understood with reference to Table A below.

TABLE A

| Sequence | Seq. ID No. | Type HPV 16, HPV 18, Probe Primer Helper | Sub-Type 1, 2 or 3 | DNA or RNA |
|---|---|---|---|---|
| GACATTATTGTTAT AGTTTGTATGGAAC | 1 | HPV 16 primer | 2 | DNA |
| GTTCCATACAAACT ATAACAATAATGTC | 2 | | | DNA |
| GACAUUAUUGUUAU AGUUUGUAUGGAAC | 3 | | | RNA |
| GUUCCAUACAAACU AUAACAAUAAUGUC | 4 | | | RNA |
| GAACAGCAATACAA CAAACCGTTGTGTG | 5 | HPV 16 probe | 3 | DNA |
| CACACAACGGTTTG TTGTATTGCTGTTC | 6 | | | DNA |
| GAACAGCAAUACAA CAAACCGUUGUGUG | 7 | | | RNA |
| CACACAACGGUUUG UUGUAUUGCUGUUC | 8 | | | RNA |
| GACGTGAGGTGTAT TAACTGTCAAAAG | 9 | HPV 16 probe | 2 | DNA |
| CTTTTGACAGTTAA TACACCTCACGTC | 10 | | | DNA |
| GACGUGAGGUGUAU UAACUGUCAAAAG | 11 | | | RNA |
| CUUUUGACAGUUAA UACACCUCACGUC | 12 | | | RNA |
| CCATGCATGATTAC AGCTGGGTTTCTC | 13 | HPV 16 primer | 2 | DNA |
| GAGAAACCCAGCTG TAATCATGCATGG | 14 | | | DNA |
| CCAUGCAUGAUUAC AGCUGGGUUUCUC | 15 | | | RNA |
| GAGAAACCCAGCUG UAAUCAUGCAUGG | 16 | | | RNA |
| TACGTGTTCTTGAT GATCTCACGTCG | 17 | HPV 16 probe | 2 | DNA |
| CGACGTGAGATCAT CAAGAACACGTA | 18 | | | DNA |
| UACGUGUUCUUGAU GAUCUCACGUCG | 19 | | | RNA |
| CGACGUGAGAUCAU CAAGAACACGUA | 20 | | | RNA |
| GTGTGTACTGCAAG CAACAGTTACTG | 21 | HPV 16 primer | 2 | DNA |
| CAGTAACTGTTGCT TGCAGTACACAC | 22 | | | DNA |
| GUGUGUACUGCAAG CAACAGUUACUG | 23 | | | RNA |
| CAGUAACUGUUGCU UGCAGUACACAC | 24 | | | RNA |

TABLE A-continued

| Sequence | Seq. ID No. | Type HPV 16, HPV 18, Probe Primer Helper | Sub-Type 1, 2 or 3 | DNA or RNA |
|---|---|---|---|---|
| CTTTTGACAGTTAA TACACCTCACG | 25 | HPV 16 probe | 3 | DNA |
| CGTGAGGTGTATTA ACTGTCAAAAG | 26 | | | DNA |
| CUUUUGACAGUUAA UACACCUCACG | 27 | | | RNA |
| CGUGAGGUGUAUUA ACUGUCAAAAG | 28 | | | RNA |
| AAAGTCATATACCT CACGTCGC | 29 | HPV 16 probe | 2 | DNA |
| GCGACGTGAGGTAT ATGACTTT | 30 | | | DNA |
| AAAGUCAUAUACCU CACGUCGC | 31 | | | RNA |
| GCGACGUGAGGUAU AUGACUUU | 32 | | | RNA |
| GAAACCCAGCTGTA ATCATGC | 33 | HPV 16 probe | 1 | DNA |
| GCATGATTACAGCT GGGTTTC | 34 | | | DNA |
| GAAACCCAGCUGUA AUCAUGC | 35 | | | RNA |
| GCAUGAUUACAGCU GGGUUUC | 36 | | | RNA |
| GATCATCAAGAACA CGTAG | 37 | HPV 16 primer | 1 | DNA |
| CTACGTGTTCTTGA TGATC | 38 | | | DNA |
| GAUCAUCAAGAACA CGUAG | 39 | | | RNA |
| CUACGUGUUCUUGA UGAUC | 40 | | | RNA |
| GGAACTGAACACTT CACTGCAAGACATA GAAATAACC | 41 | HPV 18 primer | 3 | DNA |
| GGTTATTTCTATGT CTTGCAGTGAAGTG TTCAGTTCC | 42 | | | DNA |
| GGAACUGAACACUU CACUGCAAGACAUA GAAAUAACC | 43 | | | RNA |
| GGUUAUUUCUAUGU CUUGCAGUGAAGUG UUCAGUUCC | 44 | | | RNA |
| GGAAAAACTAACTA ACACTGGGTTATAC AAT | 45 | HPV 18 probe | 1 | DNA |
| ATTGTATAACCCAG TGTTAGTTTTTCC | 46 | | | DNA |
| GGAAAAACUAACUA ACACUGGGUUAUAC CAU | 47 | | | RNA |
| AUUGUAUAACCCAG UGUUAGUUUUUCC | 48 | | | RNA |
| CATAGAAATAACCT GTGTATATTGCAAG | 49 | HPV 18 primer | 2 | DNA |
| CTTGCAATATACAC AGGTTATTTCTATG | 50 | | | DNA |
| CAUAGAAAUAACCU GUGUAUAUUGCAAG | 51 | | | RNA |
| CUUGCAAUAUACAC AGGUUAUUUCUAUG | 52 | | | RNA |
| GACATTATTCAGAC TCTGTGTATGGAG | 53 | HPV 18 primer | 2 | DNA |
| CTCCATACACAGAG TCTGAATAATGTC | 54 | | | DNA |
| GACAUUAUUCAGAC UCUGUGUAUGGAG | 55 | | | RNA |
| CUCCAUACACAGAG UCUGAAUAAUGUC | 56 | | | RNA |
| GCAAGACAGTATTG GAACTTACAGAG | 57 | HPV 18 probe | 3 | DNA |
| CTCTGTAAGTTCCA ATACTGTCTTGC | 58 | | | DNA |
| GCAAGACAGUAUUG GAACUUACAGAG | 59 | | | RNA |
| CUCUGUAAGUUCCA AUACUGUCUUGC | 60 | | | RNA |
| CCTGTGTATATTGC AAGACAGTATTG | 61 | HPV 18 helper | 2 | DNA |
| CAATACTGTCTTGC AATATACACAGG | 62 | | | DNA |
| CCUGUGUAUAUUGC AAGACAGUAUUG | 63 | | | RNA |
| CAAUACUGUCUUGC AAUAUACACAGG | 64 | | | RNA |
| GAACTTACAGAGGT ATTTGAATTTGC | 65 | HPV 18 probe | 3 | DNA |
| GCAAATTCAAATAC CTCTGTAAGTTC | 66 | | | DNA |
| GAACUUACAGAGGU AUUUGAAUUUGC | 67 | | | RNA |
| GCAAAUUCAAAUAC CUCUGUAAGUUC | 68 | | | RNA |
| CAACCGAGCACGAC AGGAACGAC | 69 | HPV 18 primer | 2 | DNA |
| GTCGTTCCTGTCGT GCTCGGTTG | 70 | | | DNA |

TABLE A-continued

| Sequence | Seq. ID No. | Type HPV 16, HPV 18, Probe Primer Helper | Sub-Type 1, 2 or 3 | DNA or RNA |
|---|---|---|---|---|
| CAACCGAGCACGAC AGGAACGAC | 71 | | | RNA |
| GUCGUUCCUGUCGU GCUCGGUUG | 72 | | | RNA |
| CCAACGACGCAGAG AAACACAAG | 73 | HPV 18 probe | 2 | DNA |
| CTTGTGTTTCTCTG CGTCGTTGG | 74 | | | DNA |
| CCAACGACGCAGAG AAACACAAG* | 75 | | | RNA |
| CUUGUGUUUCUCUG CGUCGUUGG | 76 | | | RNA |
| CTTACAGAGGTGCC TGCGGTGC | 77 | HPV 18 probe | 3 | DNA |
| GCACCGCAGGCACC TCTGTAAG | 78 | | | DNA |
| CUUACAGAGGUGCC UGCGGUGC | 79 | | | RNA |
| GCACCGCAGGCACC UCUGUAAG | 80 | | | RNA |
| GAACTTACAGAGGT GCCTGCGG | 81 | HPV 18 probe | 3 | DNA |
| CCGCAGGCACCTCT GTAAGTTC | 82 | | | DNA |
| GAACUUACAGAGGU GCCUGCGG | 83 | | | RNA |
| CCGCAGGCACCUCU GUAAGUUC | 84 | | | RNA |
| CAGGACACAGTGGC TTTTGAC | 85 | HPV 16 primer | 3 | DNA |
| GTCAAAAGCCACTG TGTCCTG | 86 | | | DNA |
| CAGGACACAGUGGC UUUUGAC | 87 | | | RNA |
| GUCAAAAGCCACUG UGUCCUG | 88 | | | RNA |
| GCTTTTTGTCCAGA TGTCTTTGC | 89 | HPV 16 primer | 2 | DNA |
| GCAAAGACATCTGG ACAAAAAGC | 90 | | | DNA |
| GCUUUUUGUCCAGA UGUCUUUGC | 91 | | | RNA |
| GCAAAGACAUCUGG ACAAAAAGC | 92 | | | RNA |
| GCAATGTAGGTGTA TCTCCATGC | 93 | HPV 16 primer | 1 | DNA |
| GCATGGAGATACAC CTACACCGC | 94 | | | DNA |
| GCAAUGUAGGUGUA UCUCCAUGC | 95 | | | RNA |
| GCAUGGAGAUACAC CUACACCGC | 96 | | | RNA |
| AATTTAATACGACT CACTATAGGGAGA | 97 | T7 Polymerase primer | 1 | DNA |
| TCTCCCTATAGTGA GTCGTATTAAATT | 98 | | | DNA |
| AAUUUAAUACGACU CACUAUAGGGAGA | 99 | | | RNA |
| UCUCCCUAUAGUGA GUCGUAUUAAAUU | 100 | | | RNA |
| TCGTTTTTCATTAA GGTGTCTAAGTTTT TCTGCTGGATTC | 101 | HPV 18 primer | 1 | DNA |
| GAATCCAGCAGAAA AACTTAGACACCTT AATGAAAAACGA | 102 | | | DNA |
| UCGUUUUUCAUUAA GGUGUCUAAGUUUU UCUGCUGGAUUC | 103 | | | RNA |
| GAAUCCAGCAGAAA AACUUAGACACCUU AAUGAAAAACGA | 104 | | | RNA |
| GCAATGTTGCCTTA GGTCCATGC | 105 | HPV 18 primer | 2 | DNA |
| GCATGGACCTAAGG CAACATTGC | 106 | | | DNA |
| GCAAUGUUGCCUUA GGUCCAUGC | 107 | | | RNA |
| GCAUGGACCUAAGG CAACAUUGC | 108 | | | RNA |
| CGGTTTCTGGCACC GCAGGCAC | 109 | HPV 18 primer | 2 | DNA |
| GTGCCTGCGGTGCC AGAAACCG | 110 | | | DNA |
| CGGUUUCUGGCACC GCAGGCAC | 111 | | | RNA |
| GUGCCUGCGGUGCC AGAAACCG | 112 | | | RNA |
| GCAATGTAGCCGTA TGTCCATGC | 113 | HPV 18 primer | 2 | DNA |
| GCATGGACATACGG CTACATTGC | 114 | | | DNA |
| GCAAUGUAGCCGUA UGUCCAUGC | 115 | | | RNA |
| GCAUGGACAUACGG CUACAUUGC | 116 | | | RNA |

TABLE A-continued

| Sequence | Seq. ID No. | Type HPV 16, HPV 18, Probe Primer Helper | Sub-Type 1, 2 or 3 | DNA or RNA |
|---|---|---|---|---|
| CACTTCACTGCAAG ACATAGAAATAACC TGTGTATATT | 117 | HPV 18 HELPER | 3 | DNA |
| AATATACACAGGTT ATTTCTATGTCTTG CAGTGAAGTG | 118 | | | DNA |
| CACUUCACUGCAAG ACAUAGAAAUAACC UGUGUAUAUU | 119 | | | RNA |
| AAUAUACACAGGUU AUUUCUAUGUCUUG CAGUGAAGUG | 120 | | | RNA |
| TTATTAATAAGGTG CCTGCGGTGCCAGA AACC | 121 | HPV 18 HELPER | 2 | DNA |
| GGTTTCTGGCACCG CAGGCACCTTATTA ATAA | 122 | | | DNA |
| UUAUUAAUAAGGUG CCUGCGGUGCCAGA AACC | 123 | | | RNA |
| GGUUUCUGGCACCG CAGGCACCUUAUUA AUAA | 124 | | | RNA |
| GACTCTGTGTATGG AGACACATT | 125 | HPV 18 HELPER | 1 | DNA |
| AATGTGTCTCCATA CACAGAGTC | 126 | | | DNA |
| GACUCUGUGUAUGG AGACACAUU | 127 | | | RNA |
| AAUGUGUCUCCAUA CACAGAGUC | 128 | | | RNA |

Preferably, the target region comprises a sequence selected from the group consisting of those set forth in SEQ ID NOs: 9-12, 17-20, 29-32, 33-36, 45-48, and 73-76, or wherein said target region consists of a sequence present in a sequence selected from the group of consisting of those set forth in SEQ ID NOs: 5-8, 25-28, 57-60, 65-68, 77-80, and 81-84. Preferred oligonucleotides have, consist essentially of, consist of, or are substantially similar to the sequences set forth in SEQ ID NOs SEQ ID NOs: 5-12, 17-20, 25-36, 45-48, 57-60, 65-68 and 73-84.

The probes are isolated nucleic acids. The term "isolated nucleic acid" means an oligonucleotide or nucleic acid molecule which is present in a form not found in nature without human intervention (e.g., recombined with foreign nucleic acid, synthesized, isolated, or purified to some extent). Preferably an isolated nucleic acid is at least 75% homogenous. The probes may also contain additional nucleotides complementary to nucleic acid sequences contiguous to the target region and may also contain nucleotides not complementary to the targeted region, so long as such additional nucleotides do not prevent hybridization under stringent hybridization conditions. Non-complementary sequences, such as a promoter sequence, a binding site for RNA transcription, a restriction endonuclease recognition site, or sequences which will confer a desired secondary or tertiary structure such as a catalytic active site can be used to facilitate detection and/or amplification.

By "oligonucleotide," "nucleotide polymer" or "nucleic acid" is meant two or more nucleotide subunits covalently joined together. The sugar groups of the nucleotide subunits may be ribose, deoxyribose, or modified derivatives thereof such as 2'O-methyl ribose. The nucleotide bases may be modified by non-nucleotide moieties, that do not prevent preferential hybridization of the oligonucleotide to its complementary target nucleic acid. The nucleotide subunits may be joined by linkages such as phosphodiester linkages, modified linkages or by non-nucleotide moieties, that do not prevent preferential hybridization of the oligonucleotide to its complementary target nucleic acid. Modified linkages include those linkages in which a standard phosphodiester linkage is replaced with a different linkage, such as a phosphothionate linkage, or methylphosphonate linkage.

By "selective stringency hybridization conditions" is meant a set of parameters which allows the probes and target sequences of the invention to hybridize to one another forming a detectable probe:target duplex which can be used to distinguish HPV type 16 and or 18 from HPV types 6, 11, 31, 33, 35, 39, 45, 51, 52, or 58 or other HPV variants. A detailed description of these parameters is provided below in the "Description of the Preferred Embodiments" subsection IC. entitled, "Construction and Use of Hybridization Assay Probes." As but one example, the selective stringency hybridization conditions may preferably comprise 0.10M to 0.14M phosphate buffer containing approximately equimolar amounts of $Na_2HPO_4$ and $NaH_2PO_4$, approximately 1 mM EDTA, and 0.01 to 0.03% sodium dodecyl sulfate at 60 to 70° C.

In preferred embodiments the target region:
(a) comprises a sequence selected from the group consisting of those set forth in SEQ ID 9-12, 17-20, 29-32, and 33-36 or consists of a sequence selected from the group of consisting of those set forth in SEQ ID NOs: 5-8, and 25-28;
(b) comprises a sequence selected from the group consisting of those set forth in SEQ ID NOs: 45-48, and 73-76, or consists of a sequence selected from the group of consisting of those set forth in SEQ ID NOs: 57-60, 65-68, 77-80, and 81-84;
(c) is DNA or RNA;
(d) comprises a sequence selected from the group of consisting of those set forth in SEQ ID NOs: 33-36, and 45-48,
(e) comprises a sequence selected from the group consisting of those set forth in SEQ ID NOs: 9-12, 17-20, 29-32, and 73-76; and/or
(f) consists of a sequence selected from the group consisting of those set forth in SEQ ID NOs: 5-8, 25-28, 57-60, 65-68, 77-80, and 81-84.

In other especially preferred embodiments the probe preferentially hybridizes to nucleic acid of HPV Type 16 and/or Type 18 and not to HPV Types 6, 11, 31, 33, 35, 39, 45, 51, 52, and/or 58 at 50 to 60° C. in 0.04M to 0.06M lithium succinate buffer containing between 0.9 and 1.1% lithium lauryl sulfate, wherein said hybrid is stable for the detection of HPV Type 16 and/or Type 18 and not for the detection of HPV Types 6, 11, 31, 33, 35, 39, 45, 51, 52, and/or 58.

The term "preferentially hybridize" is meant to indicate that under stringent hybridization assay conditions, hybridization assay probes can hybridize to their target nucleic acids to form stable probe:target hybrids which can be detected to indicate the presence of the target nucleic acid while the probes do not form a sufficient number of stable probe:non-target hybrids under these conditions to indicate the presence of a closely related non-target nucleic acid. Organisms "closely related" to HPV Types 16 and/or Type 18 include HPV Types 6, 11, 31, 33, 35, 39, 45, 51, 52, or 58 (see, Van Ranst et al., *J. Gen Vir.*, 73:2653-60, 1992).

Preferably the oligonucleotide comprises a sequence which is at least 90% complementary to said target sequence of 10 or more contiguous nucleotides, more preferably the oligonucleotide comprises a sequence which is 100% complementary to said target sequence of 10 or more contiguous nucleotides. In yet other preferred embodiments the oligonucleotide is 10 to 100 nucleotides in length, 14 to 50 bases in length, up to 40 nucleotides in length, 23-40 bases in length. The oligonucleotide may be linked to a second oligonucleotide sequence which is recognized by an RNA polymerase or which enhances initiation or elongation by an RNA polymerase.

II. Nucleic Acid Hybrids

Another aspect of the present invention relates to compositions containing detectable nucleic acid hybrids made up of a hybridization assay probe and an HPV nucleic acid molecule having a nucleic acid sequence substantially complementary thereto. The hybrid is a stable nucleic acid structure comprising a double-stranded, hydrogen-bonded region, preferably 10 to 100 nucleotides in length. The term "hybrids" include RNA:RNA, RNA:DNA, or DNA:DNA duplex molecules. The hybridization probe present in the nucleic acid hybrid has one of the sequences noted above.

The term "substantially complementary" means that the nucleic acid sequence is able to preferentially hybridize under stringent hybridization assay conditions to a target nucleic acid region. Preferably, the probe has a region of at least 10 contiguous nucleotide bases which are complementary to the corresponding target region. More preferably, the probe has a region of at least 14 contiguous nucleotide bases which are complementary to the corresponding target region.

The hybrid preferably is stable for the detection of HPV Type 16 and/or Type 18 and not for the detection of HPV Types 6, 11, 31, 33, 35, 39, 45, 51, 52, and/or 58 and may further comprise a site for the initiation of nucleic acid synthesis. Under stringent hybridization conditions said oligonucleotide preferably hybridizes specifically to nucleic acid of HPV Type 16 and/or Type 18 and not to HPV Types 6, 11, 31, 33, 35, 39, 45, 51, 52, or 58.

III. Helper Probes

In another aspect the invention features helper probes comprising an oligonucleotide, wherein said oligonucleotide comprises a sequence which will hybridize to a target sequence, wherein said target sequence has, consists essentially of, consists of, or is substantially similar to a sequence selected from the group consisting of SEQ ID NOs: 62, 64, 118, 120, 122, 124, 126, and 128.

In preferred embodiments, the oligonucleotide is substantially identical to (at least 70%) at least 10 contiguous nucleotides in a sequence selected from the group consisting of SEQ ID NOs: 61, 63, 117, 119, 121, 123, 125, and 127. In particular preferred embodiments the helper probes consist of these sequences.

It is also preferred that the oligonucleotide is at least 90% complementary to said subsequence of 10 or more contiguous nucleotides and more preferably is 100% complementary to said subsequence of 10 or more contiguous nucleotides. The oligonucleotide is preferably 10 to 100 nucleotides in length, 15 to 50 bases in length, up to 40 nucleotides in length, or 23-40 bases in length.

The preferred oligonucleotides have, consist essentially of, consist of, or are substantially similar to the sequences set forth in SEQ ID NOs: 61, 63, 117, 119, 121, 123, 125 and 127.

IV. Probe Mixes

Another aspect of the invention features probe mixes containing at least one hybridization probe and at least one helper probe for use in a hybridization assay. Helper probes can be used to facilitate hybridization of the probe:target duplex in a hybridization assay. Helper probes facilitate hybridization by enhancing the kinetics and/or the Tm of the target:hybridization probe duplex. Helper probes are described in Hogan and Milliman, U.S. Pat. No. 5,030,557, which is incorporated by reference herein in its entirety, including any drawings.

Specifically, helper oligonucleotides are designed to bind to the target nucleic acid and impose a different secondary and tertiary structure on the target to facilitate binding of the assay probe to the target. The resulting hybrid of assay probe and target nucleic acid also exhibits a higher $T_m$ than the hybrid which results from addition of the probe in the absence of helper oligonucleotides. Because a substantial portion of this secondary and tertiary structure is not lost under conditions normally employed for nucleic acid hybridization, e.g., elevated temperature, presence of salt, presence of accelerators and the like, this residual structure can sterically inhibit, or even block, hybrid formation between a nucleotide multimer, for example a DNA or RNA oligomer being used as a probe, and its complementary sequence in the ribosomal RNA or other single-stranded nucleic acid such as mRNA or DNA which the probe targets. This inhibition can be reduced and even eliminated, by use of a "helper" oligonucleotide which binds to a portion of the RNA or DNA other than that being targeted by the probe, and which imposes new secondary and tertiary structure on the targeted region of the single-stranded nucleic acid whereby the rate of binding of the probe is accelerated. Thus, the rate of hybridization can be substantially increased and even permit hybridization to occur at a rate and under conditions otherwise adequate for an assay where, without the use of the helper, no substantial hybridization can occur.

In a preferred embodiment, nucleic acid hybridization assay probe component of the probe mix can detect the presence of HPV Type 16 and/or Type 18 and comprises a first oligonucleotide 10 to 100 bases in length having at least 14 out of 17 contiguous bases perfectly complementary to a first nucleic acid target region that consist of a sequence selected from the group consisting of those set forth in SEQ ID NOs: 9, 11, 17, 19, 29, 31, 33, 35, 45, 47, 73, and 75 or consists of a sequence selected from the group of consisting of those set forth in SEQ ID NOs: 5, 7, 25, 27, 57, 59, 65, 67, 77, 79, 81, and 83. The hybridization assay probe preferably distinguishes HPV Type 16 and/or Type 18 from HPV Types 6, 11, 31, 33, 35, 39, 45, 51, 52, and/or 58 under selective hybridization conditions, i.e., under said conditions said hybridization assay probe hybridizes to HPV Type 16 and/or Type 18 RNA or DNA to form a detectable probe:target duplex, but does not hybridize to non-target nucleic acid from HPV 6, 11, 31, 33, 35, 39, 45, 51, 52, and/or 58 to form a detectable probe:non-target duplex.

Also in preferred embodiments the helper probe component of the probe mix comprises a second oligonucleotide which is at least 70% complementary to a second target sequence that comprises a sequence selected from the group consisting of those set forth in SEQ ID NOs: 61, 63, 121, 123, 125 and 127 or consists of a sequence selected from the group of consisting of those set forth in SEQ ID NOs: 117 and 119.

With respect to a hybridization assay probe or a helper probe, a "substantially similar" nucleotide sequence is a nucleotide sequence identical to, or having no more than a 10% nucleotide base difference than an identified nucleotide sequence (excluding substitution of a RNA or DNA equivalent nucleotide, e.g., substituting T for U or U for T) and which enables a hybridization assay probe or helper probe to hybridize to HPV Type 16 and/or Type 18 nucleic acid under stringent hybridization conditions used to detect HPV Type 16 and/or Type 18. With respect to amplification oligonucleotides, a "substantially similar" nucleotide sequence is a nucleotide sequence identical to, or having no more than a 20% nucleotide base difference than an identified nucleotide sequence (excluding substitution of a RNA or DNA equivalent nucleotide, e.g., substituting T for U or U for T) and which enables an amplification oligonucleotide to prime or initiate the amplification of HPV target nucleic acid under amplification conditions.

The phrases "consists essentially of" or "consisting essentially of" mean that the oligonucleotide has a nucleotide sequence substantially similar to a specified nucleotide sequence and is preferably no more than four additional nucleotides longer or two nucleotides shorter. Thus, these phrases contain both a sequence length limitation and a sequence variation limitation. Any additions, substitutions or deletions of an oligonucleotide consisting essentially of the specified nucleotide sequence do not deprive it of its basic and novel properties, vis, the ability to specifically hybridize with its target and function as a probe or a primer. For instance, with respect to hybridization and helper probes, any additions, substitutions or deletions would not prevent these probes from being able to preferentially hybridize under stringent hybridization assay conditions to its target nucleic acid over non-target nucleic acids. With respect to an amplification oligonucleotide, any additions, substitutions or deletions would not prevent it from being able to prime amplification reactions producing target HPV nucleic acid under amplification conditions.

V. Amplification Oligonucleotides

In another aspect, the invention features an amplification oligonucleotide for amplifying HPV Type 16 and/or Type 18 nucleic acid sequences. The oligonucleotide comprises a sequence of nucleic acids which has a region that is at least 70% complementary to a subsequence of 10 or more contiguous nucleic acids present in target sequence. The target sequence has, consists essentially of, consists of, or is substantially similar to a sequence selected from the group consisting of those set forth in SEQ ID NOs: 2, 4, 14, 16, 22, 24, 38, 40, 42, 44, 50, 52, 54, 56, 70, 72, 86, 88, 90, 92, 94, 96, 102, 104, 106, 108, 110, 112, 114, and 116.

In preferred embodiments, the oligonucleotide is DNA or RNA at least 70% identical to a subsequence of 10 or more contiguous nucleotides present in: (a) a sequence selected from the group of consisting of those set forth in SEQ ID NOs: 37, 39, 93, 95, 101, and 103; (b) a sequence selected from the group consisting of those set forth in SEQ ID NOs: 1, 3, 9, 11, 13, 15, 21, 23, 49, 51, 53, 55, 69, 71, 89, 91, 105, 107, 109, 111, 113, and 115; or (c) a sequence selected from the group consisting of those set forth in SEQ ID NOs: 41, 43, 85, and 87. The oligonucleotide is preferably at least 90% identical to said subsequence of 10 or more contiguous nucleotides, more preferably 100% identical to said subsequence of 10 or more contiguous nucleotides. The oligonucleotide is preferably 10 to 100 nucleotides in length, 15 to 50 bases in length, up to 40 nucleotides in length, or 23-40 bases in length.

In another aspect, the invention features amplification oligonucleotides useful for binding to, extending through, or transcribing HPV target regions. Located at the 5' end of the amplification oligonucleotide, which acts as a promoter sequence, is a sequence which is recognized by an RNA polymerase or which enhances initiation or elongation by an RNA polymerase. Located at the 3' end of the same amplification oligonucleotide, is one or more sequences which acts as a target hybridizing region to HPV type 16 and or 18.

"RNA and DNA equivalent nucleotides" refer to RNA and DNA molecules having the equivalent base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially similar nucleic acid base sequences.

Amplification oligonucleotides are preferably 10 to 100 nucleotides in length, more preferably 22 to 44 nucleotides. Amplification oligonucleotides may have modifications, such as blocked 3' and/or 5' termini or additions including, but not limited to, specific nucleic acid sequences recognized by an RNA polymerase, (e.g., the promoter sequence for T7, T3, or SP6 RNA polymerase) sequences enhancing initiation or elongation of RNA transcription by an RNA polymerase (Kacian et al., U.S. Pat. No. 5,399,491 incorporated herein in its entirety including drawings).

Amplification oligonucleotides can be used in nucleic acid amplification procedures, such as the polymerase chain reaction or transcription associated amplification reactions, such as that using RNA polymerase, and reverse transcriptase, as described by Kacian and Fultz, supra. Other transcription based amplification systems are described in Sninsky et al., U.S. Pat. No. 5,079,351. Both of these references are hereby incorporated by reference herein. Preferably, promoters which are recognized by an RNA polymerase such as T7, T3 or SP6 RNA polymerase are used for the transcription-based amplification.

The term "amplification" means increasing the number of nucleic acid molecules having at least one specific target nucleic acid sequence. In order to increase the amplification of oligonucleotides containing target sequences, applicants preferably employ amplification systems in which target-template strands containing a double-stranded promoter region are produced to serve as templates for RNA polymerase. The target-template amplification is preferably carried out using a primer recognized by the DNA polymerase activity of reverse transcriptase.

VI. Methods of Amplification and Detection

In another aspect the invention provides a method for selectively amplifying HPV Type 16 and/or Type 18 nucleic acid in a sample by amplifying the nucleic acid with one or more probes of the invention.

In yet another aspect the invention features a method for detecting HPV Type 16 and/or Type 18 in a sample potentially containing the HPV Type 16 and/or Type 18 comprising the steps of:

a) providing to said sample one or more nucleic acid hybridization assay probes of the invention; and b) detecting the formation of said detectable probe:target duplex which is indicative of the presence of HPV Type 16 and/or Type 18.

In a preferred embodiment the target nucleic acid is amplified with an amplification probe and detected with a detection probe. Examples of most preferred combinations of a particular amplification probe with a particular detection probe (i.e., the best-mix combination) are shown in the examples presented herein.

In other aspects, methods are described for using the hybridization assay probes, helper probes and amplification oligonucleotides to detect HPV Type 16 and/or Type 18 and to distinguish HPV Type 16 and/or Type 18 from closely related organisms. These amplification assays involve amplifying target nucleic acid in a sample to be tested, contacting the amplified sequences under stringent hybridization assay conditions with a hybridization assay probe which preferentially hybridizes with HPV Type 16 and/or Type 18 nucleic acid over nucleic acids present in closely related organisms, and detecting or measuring the hybridized probe.

The sample is preferably a clinical sample such as sputum, urine, blood, uro-genital secretion, clinical swabs, tissue sections or nucleic acid isolated from a clinical sample. More preferably, the amplification assay will be used to detect HPV Type 16 and/or Type 18 directly from a clinical sample. Detection directly from a clinical sample means that culture of the sample is not required prior to carrying out the amplification assay.

Preferably the amplification assay utilizes a hybridization probe consisting of one those listed above.

Helper probes for use in preferred embodiments of the amplification assay have, or are substantially similar to sequences selected from the group of Seq ID NOS: 117-128.

VII. Kits

The present invention also features a kit containing one or more of the hybridization assay probes or probe mixes of the invention. A kit contains all the necessary reagents to carry out the methods of detection described herein, for example one or amplification oligonucleotides or helper probes described herein. The kit may contain a one or more container means, a product insert label, and/or a buffer solution. Those skilled in the art will recognize that the probes of the present invention can readily be incorporated into one of the established kit formats which are well known in the art.

The oligonucleotides targeted to HPV offer a rapid, objective and sensitive method of identification and quantitation of HPV by detecting the presence of specific nucleic acid sequences unique to different species and strains of HPV Type 16 and/or Type 18. The probes of this invention can be used to identify, in hybridization assays, HPV from clinical samples. Combining an amplification step with a hybridization assay in the amplification assay increases the amount of target and thus the sensitivity of the assay. Both HPV type 16 and 18 can be amplified and detected in the same reaction vessel. A specially designed mismatch primer can amplify HPV Type 16 and/or Type 18 separately or simultaneously in the same reaction vessel. Probes can detect unspliced and heterogenous mRNA splices of HPV Type 16 and/or Type 18. Some of the probes of the present invention have been designed to exclude detection of mRNA targets which may be advantageous in certain applications.

Other features and advantages of the invention will be apparent from the following description of the preferred embodiments thereof, and from the claims.

DESCRIPTION OF THE PREFERRED EMBODIMENTS

Following is description of HPV nucleic acids, methods of making and using oligonucleotide probes, and kits containing such probes. In particular, different types of oligonucleotide probes are described (including hybridization assay probes, helper oligonucleotides and amplification oligonucleotides) which are useful for detecting HPV Type 16 or Type 18 in a clinical sample, such as a vaginal swab, a cervical swab, a urethral swab, a tissue sample, a body fluid or an experimental solution.

Figure 1:
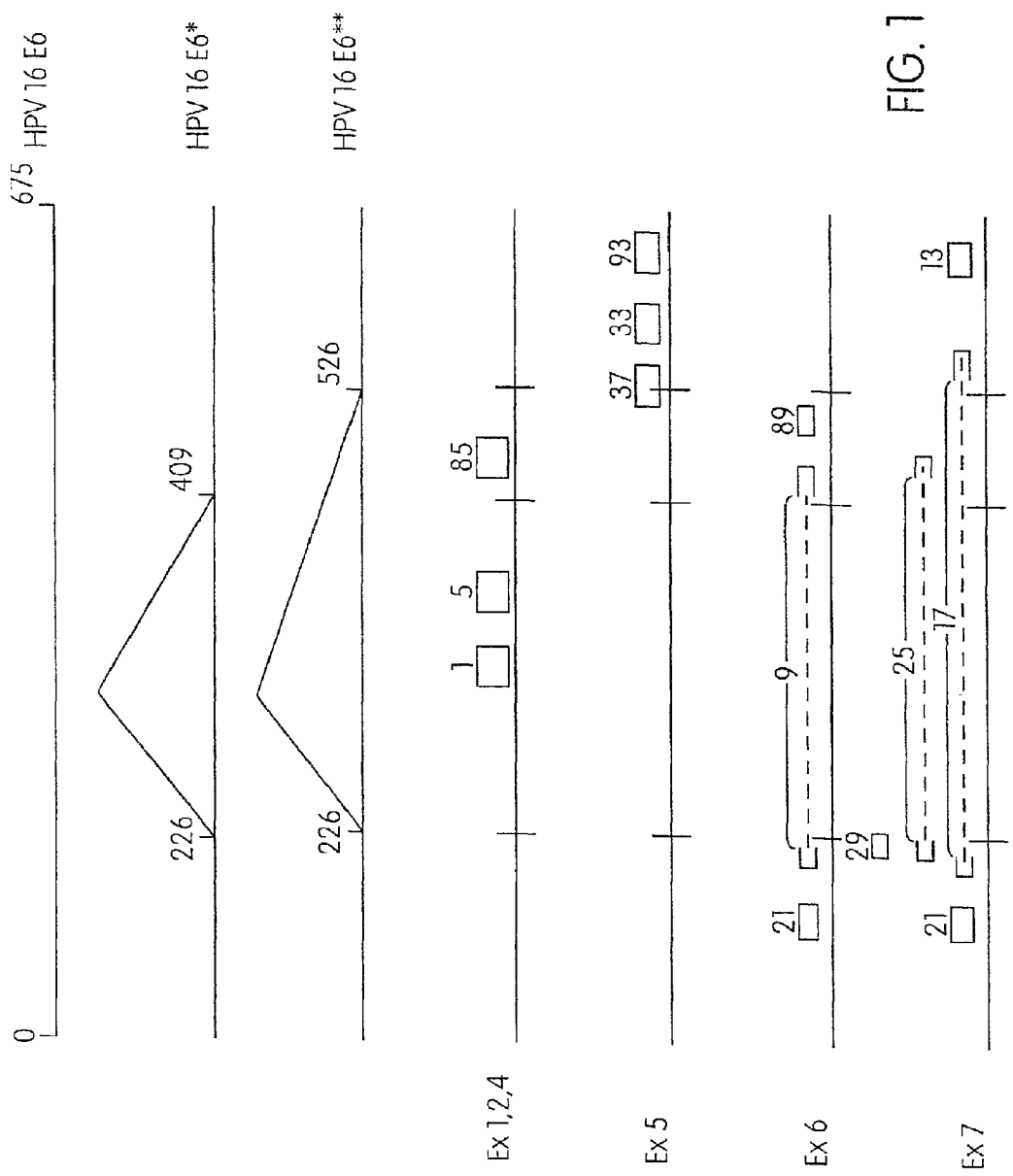
FIGS. 1 and 2 are representations respectively of the E6 region in the HPV Type 16 and HPV Type 18 genome. The top line represents that portion of the genome between the designated base pairs (vertical lines). Subsequently lower lines show splice acceptor sites and that portion of mRNA excised during transcription to produce either the E6* or E6** species of mRNA (area excised underlies triangle; i.e., in FIG. 1 the area between bases 233-416 of the HPV type 18 RNA is excised during transcription resulting in the E6*mRNA). Still lower lines represent preferred probes, primers, and amplifying oligonucleotides (rectangles with SEQ ID NOS. adjacent) that were used in the Examples section below, i.e., which were used in amplifying and detecting either HPV type 16 or HPV type 18 E6, E6*, or E6** mRNA (specific example numbers located left of line).
Figure 2:
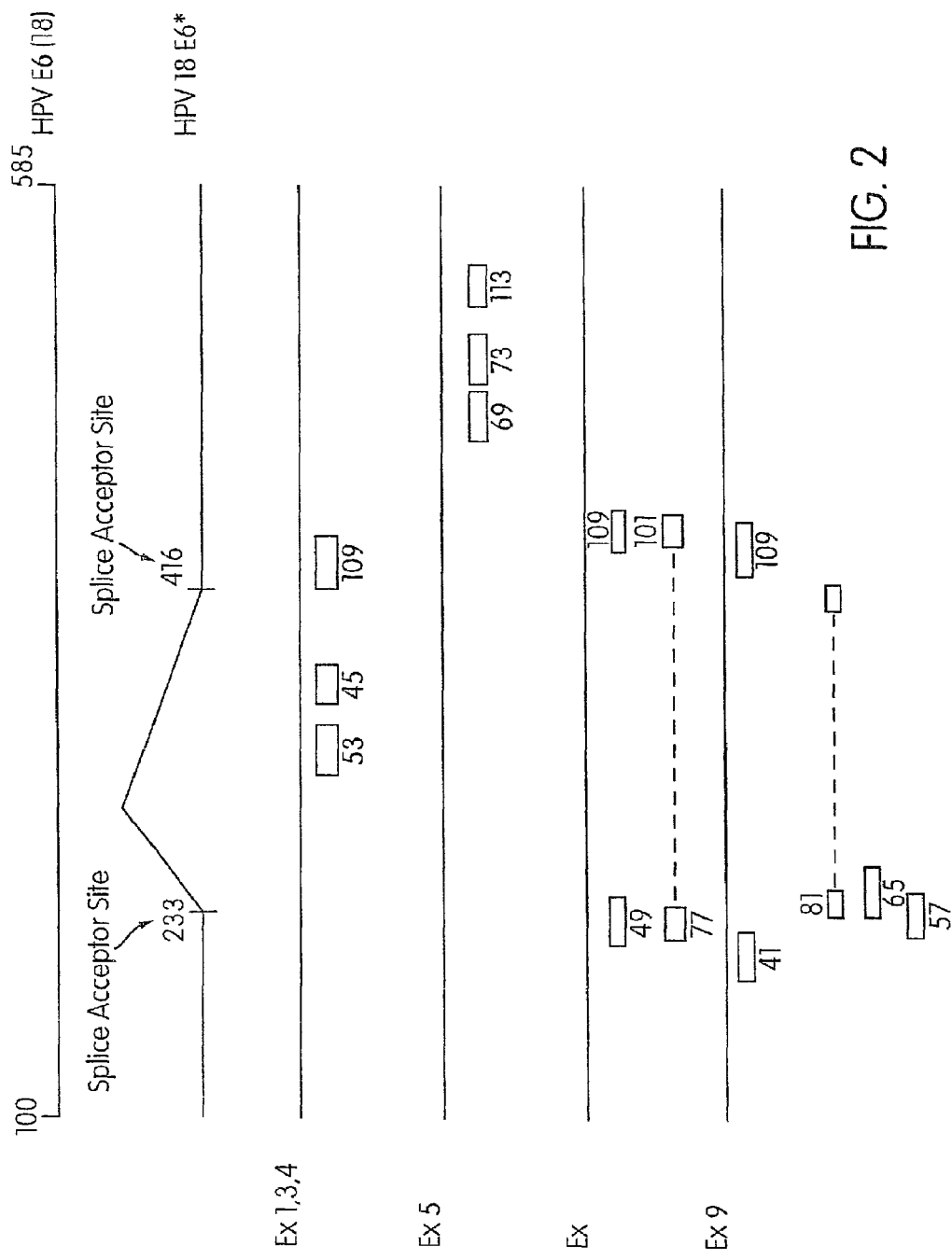

I. Construction And Use Of Hybridization Assay Probes

A. Probe Design

Strands of deoxyribonucleic acid ("DNA") or ribonucleic acid ("RNA") are formed from nucleotide units joined in a specific arrangement, or sequence. Nucleotides each contain one "base" structure and are distinguished from one another by the base which they contain. Bases include adenine (A), cytosine (C), thymine (T), guanine (G), uracil (U), or inosine (I)).

The structures of the bases in the nucleotides permit certain pairs of bases to interact with one another through the formation of hydrogen bonds. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs. Bases which can hydrogen bond are said to be complementary to one another.

Two single strands of DNA or RNA may specifically align and associate ("hybridize") to form a double stranded structure in which the two strands are held together by the hydrogen bonds which form between pairs of complementary bases. When a first single-strand of nucleic acid contains sufficient contiguous complementary bases to a second, and those two strands are brought together under conditions promoting their hybridization, double-stranded nucleic acid results. Under appropriate conditions, double-stranded DNA/DNA, RNA/DNA, or RNA/RNA hybrids may be formed. Conditions which decrease the likelihood of forming a given double-stranded hybrid are said to be more stringent conditions than conditions in which hybrid formation is less likely.

A probe is generally a single-stranded nucleic acid having a base sequence which is complementary to some degree to a nucleic acid oligonucleotide "target region" comprising, consisting essentially of, or consisting of a "target sequence" sought to be detected. It may contain a detectable moiety such as a radioisotope, antigen or chemiluminescent moiety. A background description of the use of nucleic acid hybridization as a procedure for the detection of particular nucleic acids is described by Hogan et al., International Patent Application No. PCT/US87/03009, entitled "Nucleic Acid Probes for Detection and/or Quantitation of Non-Viral Organisms," incorporated by reference herein in its entirety, including any drawings.

Using methods known to those skilled in the art, and described herein, regions of RNA or DNA sequences from HPV Type 16 and/or Type 18 were identified. Nucleic acids from different organisms and having different nucleotide sequences can be aligned in regions of homology based on a conserved primary sequence. Potential target sequences for the hybridization assay probes described herein were identified by noting variations in the homology of the aligned sequences.

The sequence evolution at each of the regions is mostly divergent. Because of this divergence, corresponding DNA regions of more distant phylogenetic relatives of HPV Type 16 and/or Type 18 show greater differences from HPV Type 16 and/or Type 18 RNA or DNA than do the DNAs of phylogenetically closer relatives. Sufficient variation between HPV Type 16 and/or Type 18 and its closest know phylogenetic relatives, HPV 6, 11, 31, 33, 35, 39, 45, 51, 52, or 58, was observed to allow identification of prospective target sites and to design hybridization assay probes useful for distinguishing between the nucleic acids of these organisms.

B. Oligonucleotide Probes

We have designed hybridization assay probes specific for HPV Type 16 and/or Type 18, and we have successfully used those probes in a specific assay for the detection of HPV Type 16 and/or Type 18, distinguishing the strains from each other and what are believed to be their most closely related taxonomic or phylogenetic neighbors. These probes have also been shown to function in an amplification assay for HPV Type 16 and/or Type 18. In addition, in a more preferred embodiment, we have used the probes in an amplification assay to detect HPV Type 16 and/or Type 18 directly from clinical samples such as vaginal swabs, sputum, biopsies, tissues, uro-genital fluid, uro-genital washes. In addition, the probes can be used to detect HPV Type 16 and/or Type 18 in other clinical samples such as blood, and tissue sections, and in other samples such as swabs, secretions or biopsies. The featured probes preferably comprises, consists essentially of, or consist of one of the sequences identified above.

As illustrated by examples described below, the described hybridization assay probes can detect HPV Type 16 and/or Type 18 and distinguish it from HPV 6, 11, 31, 33, 35, 39, 45, 51, 52, or 58.

C. Hybridization

Hybridization assay probes and helper probes hybridize to their target sequence under stringent hybridization conditions. Oligonucleotides acting as helper probes or amplification oligonucleotides do not need to be able to preferentially hybridize to HPV Type 16 and/or Type 18 nucleic acid.

Preferential hybridization of hybridization assay probes to their target nucleic acids can be accomplished by choosing the appropriate hybridization assay conditions and proper probe design. The stability of the probe:target nucleic acid hybrid should be chosen to be compatible with the assay and washing conditions so that stable, detectable hybrids form only between nucleic acids having highly complementary sequences. Manipulation of one or more of the different assay parameters determines the exact sensitivity and specificity of a particular hybridization assay probe.

Preferential hybridization occurs under stringent hybridization assay conditions. In general, reducing the degree of complementarity of an oligonucleotide targeted region to its target sequence region decreases the degree or rate of hybridization of the probe oligonucleotide to its target sequence region.

Preferential hybridization can be measured using techniques known in the art and described herein, such as in the examples provided below. Preferably, there is at least a 100-fold difference between target and non-target hybridization signals, more preferably at least a 1,000-fold difference, even more preferably at least a 10,000-fold difference. Also preferably, non-target hybridization signals are not more than background level.

The following guidelines are useful for designing probes and determining specific stringent hybridization assay conditions. Because the sensitivity and specificity of hybridization reactions such as those described herein are affected by a number of factors, including the hybridization assay probe nucleotide sequence and length, the sequence of the target sequence region, the degree of homology between the target sequence and the analogous aligned HPV nucleic acid sequences from closely related organisms, the hybridization temperature, and the composition of hybridization reagents, the manipulation of one or more of those factors will determine the exact sensitivity and specificity of a particular probe, whether perfectly complementary to its target or not. The importance and effect of various hybridization assay conditions, explained further herein, are known to those skilled in the art.

First, the stability of the probe:target nucleic acid hybrid should be chosen to be compatible with the assay conditions so that stable, detectable hybrids form only between nucleic acids having highly complementary sequences. Probes should be designed to have an appropriate melting temperature (Tm). This may be accomplished by varying the probe length and nucleotide composition (percentage of G+C versus A+T). The probe length and nucleotide composition are preferably chosen to correspond to a Tm about 2-10° C. higher than the temperature at which the final assay will be performed. For instance, the Tm can be increased by avoiding long A and T rich sequences, or by terminating the hybrids with G:C base pairs. The beginning and end points of the probe should be chosen so that the length and % G+C content result in a Tm about 2-10° C. higher than the temperature at which the final assay will be performed.

In general, the optimal hybridization temperature for an oligonucleotide is approximately 5° C. below the melting temperature for a given duplex. Incubation at temperatures below the optimum temperature may allow mismatched base sequences to hybridize and can therefore decrease specificity. The longer the oligonucleotide, the more base pairs are present to hydrogen bond and, in general, the higher the Tm. The base composition of the probe is significant because G-C base pairs exhibit greater additional hydrogen bonding and therefore greater thermal stability than A-T base pairs. (See, e.g., Sambrook, et al., *Molecular Cloning: A Laboratory Manual*, 2:11 (2d ed. 1989) [hereinafter *Molecular Cloning*]) Thus, hybridization involving complementary nucleic acids of higher G-C content will be stable at higher temperatures.

To ensure specificity of a hybridization assay probe for its target, it is preferable to design probes which hybridize with target nucleic acids and not with non-target nucleic acids under conditions of high stringency. Under high stringency conditions only highly complementary nucleic acid hybrids will form. Accordingly, the stringency of the assay conditions determines the amount of complementarity which should exist between two nucleic acid strands in order to form a hybrid under those conditions. Stringency should be chosen to maximize the difference in stability between the probe:target hybrid and potential probe:non-target hybrids.

In addition, proper specificity may be achieved by minimizing the length of the hybridization assay probe having perfect complementarity to sequences of non-target organisms by minimizing the length of perfect complementarity to non-target organisms, avoiding G and C rich regions of homology to non-target sequences, and by constructing the probe to contain as many destabilizing mismatches to non-target sequences as possible. Whether a probe sequence is appropriate for detecting only a specific type of organism depends largely on the thermal stability difference between probe:target hybrids and probe:non-target hybrids. In designing probes, the differences in these Tm values should be as large as possible (e.g., at least 2° C. and preferably 5° C. or more).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs from it merely by a single base. While it is possible for nucleic acids that are not perfectly complementary to specifically hybridize, the longest stretch of perfectly homologous base sequence generally determines hybrid stability.

Third, regions of RNA which are known to form strong internal structures inhibitory to hybridization are less preferred target regions. Likewise, probes with extensive self-complementarity should be avoided. If a strand is wholly or partially involved in an intramolecular or intermolecular hybrid it will be less able to participate in the formation of a new intermolecular probe:target hybrid. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

HPV target sequences may initially be present as part of a nucleic acid duplex. For example, a genomic DNA target occurs naturally in a double stranded form. The polymerase chain reaction (PCR) and transcription-based amplification systems can also give rise to a double stranded product. These double-stranded targets require denaturation prior to hybridization. Appropriate denaturation and hybridization conditions are known in the art (e.g., E. M. Southern, *J. Mol. Biol.* 98:503 (1975)).

The rate of hybridization may be measured by determining the $C_0T_{1/2}$. The rate at which a probe hybridizes to its target is a measure of the thermal stability of the target secondary structure in the probe region. The standard measurement of hybridization rate is the $C_0T_{1/2}$ which is measured as moles of nucleotide per liter times seconds. Thus, the $C_0T_{1/2}$ value is the concentration of probe times the half-life of hybridization at that concentration. This value is determined by hybridizing various amounts of probe to a constant amount of hybrid for a fixed time.

In one example, 0.05 pmol of target is incubated with 0.0012, 0.025, 0.05, 0.1 and 0.2 pmol of probe for 30 minutes. The amount of hybrid after 30 minutes is preferably measured by using Hybridization Protection Assay as described below. The signal is then plotted as the logarithmic unit of the percent of maximum Relative Light Units (RLU) (from the highest probe concentration) versus probe concentration (moles of nucleotide per liter). RLU are a measurement of the quantity of photons emitted by the labeled-probe measured by the luminometer. The $C_0T_{1/2}$ is found graphically from the concentration corresponding to 50% of maximum hybridization multiplied by the hybridization time in seconds. These values range from $9.0\times10^{-6}$ to $9\times10^{-5}$ with the preferred values being less than $3.5\times10^{-5}$.

Other methods of nucleic acid reassociation can be used. For example, Kohne and Kacian, EP 229442, entitled "Accelerated Nucleic Acid Reassociation Method," describes a method to accelerate nucleic acid reassociation.

A preferred method to determine Tm measures hybridization using a hybridization protection assay (HPA) according to Arnold, et al., U.S. Pat. No. 5,283,171, entitled "Homogeneous Protection Assay." Tm can be measured using HPA in the following manner. Probe molecules are labeled with an acridinium ester. Probe:target hybrids are formed in a lithium succinate buffer (0.1 M lithium succinate buffer, pH 5.0, 2 mM EDTA, 2 mM EGTA, 10% (w/v) lithium lauryl sulfate) using an excess amount of target. Aliquots of the solution containing the nucleic acid hybrids are then diluted in the lithium succinate buffered solution and incubated for five minutes at various temperatures starting below that of the anticipated Tm (typically 55° C.) and increasing in 2-5° increments. This solution is then diluted with a mild alkaline borate buffer (0.15 M sodium tetraborate, pH 7.6, 5% (v/v) polyoxethylene ether (TRITON® X-100)) and incubated at a lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer (e.g., the Gen-Probe LEADER® I or LEADER® 50). The resulting data is plotted as percent of maximum signal (usually from the lowest temperature) versus temperature. The Tm is defined as the temperature at which 50% of the maximum signal remains. In addition to the method above, Tm may be determined by isotopic methods known to those skilled in the art (see e.g., Hogan et al., supra).

The Tm for a given hybrid varies depending on the nature of the hybridization solution used. Factors such as the concentration of salts, detergents, and other solutes can affect hybrid stability during thermal denaturation (see J. Sambrook, et al., supra). Conditions such as ionic strength and incubation temperature under which a probe will be used should be taken into account in constructing a probe. It is known that the thermal stability of a hybrid nucleic acid increases with the ionic strength of the reaction mixture. On the other hand, the addition of chemical reagents which disrupt hydrogen bonds, such as formamide, urea, DMSO and alcohols, can greatly reduce hybrid thermal stability and thereby increase the stringency of hybridization. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

Examples of specific stringent hybridization conditions for hybridization assay probes are provided in the examples described below. Additional sets of stringent hybridization conditions can be determined based on the present disclosure by those of ordinary skill in the art. (See e.g., *Molecular Cloning*, supra.)

D. Oligonucleotide Synthesis

Defined oligonucleotides may be produced by any of several well known methods, including automated solid-phase chemical synthesis using cyanoethylphosphoramidite precursors. Barone et al., *Nucleic Acids Res.* 12:4051 (1984). In addition, other well-known methods for construction of synthetic oligonucleotides may be employed. *Molecular Cloning*, supra (2:11). Following synthesis and purification of an oligonucleotide, several different procedures may be utilized to determine the acceptability of the oligonucleotide in terms of size and purity. Such procedures include polyacrylamide gel electrophoresis and high pressure liquid chromatography, both of which are known to those skilled in the art.

Once synthesized, selected oligonucleotide hybridization assay probes may also be labeled with a reporter group by an of several well known methods. *Molecular Cloning*, supra (2:11). Useful labels include radioisotopes as well as non-radioactive reporting groups. Isotopic labels include $^3$H, $^{35}$S, $^{32}$P, $^{125}$I, Cobalt and $^{14}$C. Isotopic labels can be introduced into an oligonucleotide by techniques known in the art such as nick translation, end labeling, second strand synthesis, reverse transcription, and by chemical methods. When using radio-labeled probes, hybridization can be detected by autoradiography, scintillation counting, or gamma counting. The chosen detection method depends on the hybridization conditions and the particular radio-isotope used for labeling.

Non-isotopic materials can also be used for labeling, and may be introduced internally between nucleotides or at an end of the oligonucleotide. Modified nucleotides may be incorporated enzymatically or chemically. Chemical modifications of the probe may be performed during or after synthesis of the probe, for example, by the use of non-nucleotide linker groups as described by Arnold et al., entitled "Non-Nucleotide Linking Reagents for Nucleotide Probes," European Pat. Appl. No. 88308766.0, Pub. No. 313219, incorporated by reference herein in its entirety including any drawings. Non-isotopic labels include fluorescent molecules, chemiluminescent molecules, enzymes, co-factors, enzyme substrates, haptens or other ligands.

Preferably, the hybridization assay probes are labeled with an acridinium ester. Acridinium ester labeling may be performed as described by Arnold et al., U.S. Pat. No. 5,185,439 entitled "Acridinium Ester Labeling and Purification of Nucleotide Probes" issued Feb. 9, 1993 and incorporated by reference herein in its entirety including any drawings.

II. Hybrids Containing a Hybridization Assay Probe and a HPV Target Sequence

Another aspect of this invention is a hybrid formed by a hybridization assay probe and a target sequence from HPV Type 16 and/or Type 18. The formed hybrid is useful for detecting the presence of the target. For example, acridinium ester ("AE") present in hybrid is resistant to hydrolysis in alkali solution while acridinium ester present in single-stranded nucleic acid is hydrolyzed in alkali solution. Thus, binding of AE-labeled probe to target can be detected, after hydrolysis of the unbound AE-labeled probe, by measuring chemiluminescence of acridinium ester remaining in the nucleic acid hybrid. Additionally, the formed hybrid can be used to as a basis to separate hybridized target from un-hybridized probe, thereby removing background due to unhybridized probe. For example, hybrid molecules can be selectively retained on hydroxyapatite columns or filters under conditions not permitting retention of single-stranded probe using methods well known to those skilled in the art (See, e.g., Sambrook, supra).

III. Mixes of Hybridization Assay Probes and Helper Probes

Mixes of hybridization assay probes and helper probes can be used in the detection of HPV Type 16 and/or Type 18. Helper probes are used to enhance the rate of nucleic acid hybridization of an assay probe with its target nucleic acid and to facilitate the hybridization of the hybridization assay probe to its target. In addition, helper probes are sufficiently complementary to their target nucleic acid sequence to form a helper probe:target duplex under stringent hybridization assay conditions. The stringent hybridization assay conditions used with a given helper probe are determined by the conditions in which a hybridization assay probe is used to preferentially hybridize to its target sequence.

Regions of single stranded RNA and DNA can be involved in secondary and tertiary structures even under stringent hybridization assay conditions. Such structures can sterically inhibit, or even block hybridization of a hybridization assay probe to its target region. Hybridization of the helper probe alters the secondary and tertiary structure of the target nucleic acid, thereby rendering the hybridization assay probe target region more accessible. As a result helper probes enhance the kinetics and/or the Tm of the target:hybridization probe duplex. Helper probes are generally selected to hybridize to nucleic acid sequences located near the hybridization assay probe target region.

Helper probes which can be used with the hybridization assay probes of the present invention are targeted to nucleic acid sequence regions of the HPV genome and will preferably contain at least 14 nucleotides of which at least 12 out of the 14 nucleotides are perfectly complementary to a nucleic acid sequence present in the HPV target region.

IV. Amplification Oligonucleotides and Amplification Assay Conditions

Methods of amplifying the number of target sequences in a sample can be combined with the use of probe sequences to increase the sensitivity of the detection assay. (Miller, et al., Evaluation of Gen-Probe Amplified *Mycobacterium Tuberculosis* Direct Test and PCR for Direct Detection of *Mycobacterium tuberculosis* in Clinical Specimens, *J. Clin. Micro.* 1994: 393-397; Reddy, et al., *Mol. Cell. Probes* 7: 121-126, 1993).

Amplification oligonucleotides can act as primers and may be part of promoter-primer combinations (i.e., a primer having an attached promoter sequence) to amplify a HPV Type 16 and/or Type 18 target sequence. Preferably the amplification oligonucleotide will have one of the following sequences: SEQ ID NOs: 1, 3, 13, 15, 21, 23, 37, 39, 41, 43, 49, 51, 53, 55, 69, 71, 89, 91, 93, 95, 101, 103, 105, 107, 109, 111, 113 and 115. In a more preferred embodiment, the amplification oligonucleotide will have one of the following sequences: SEQ ID Nos: 85, 87, 91, 93, 95, 101, 103, 105, 107, 109, 111, 113, and 115. In an even more preferred embodiment, the amplification oligonucleotide will have one of the following sequences: SEQ ID Nos: 109 and 111.

The degree of amplification observed with a set of primers or promoter-primers depends on several factors, including the ability of the oligonucleotides to hybridize to their specific target sequences and their ability to be extended or recognized by an RNA polymerase. While oligonucleotides of different lengths and base composition may be used, more preferred amplification oligonucleotides have target binding regions of 30-60 bases and a predicted hybrid Tm of about 65° C.

A target nucleic acid sequence present on a nucleic acid molecule can be amplified using an amplification oligonucleotide 5' of the target sequence and an amplification oligonucleotide 3' of the target sequence. The preferred target sites for amplification oligonucleotides are regions greater than about 14 bases in length. The amplified region, defined by the amplification oligonucleotides, is preferably about 350 bases or less in length, and more preferably about 150 bases or less in length.

Parameters affecting probe hybridization such as Tm, complementarity and secondary structure also affect primer hybridization and therefore performance of the amplification oligonucleotides. These considerations, which were discussed above in the section concerning probe design, can be modified depending upon the amplification conditions. For example, amplification can be carried out under conditions of lower stringency than diagnostic hybridization assay conditions.

The degree of non-specific extension (primer-dimer or non-target copying) can affect amplification efficiency. Primers are preferably selected to have low self-or cross complementarity, particularly at the 3' ends of the sequence. Long homopolymer tracts and high GC content are preferably avoided to reduce spurious primer extension. Computer programs are commercially available to aid in this aspect of the design.

The terms "E6", "E6*" and "E6**" refer to the open reading frame of the HPV genome which encodes the number six "early" gene. This gene is designated by the prefix letter "E" for early, in conjunction with the arabic numeral "6" for the number six. The modifying terms designated by the characters "*" or "**" refer to alternatively spliced messenger RNAs which employ alternative acceptor splice sites within the E6 region of the HPV genome. Splicing at these sites during transcription of the E6 gene, results in the production of two different species of E6 mRNA's which differ in length from the canonical E6 mRNA. Therefore, three different E6 messenger RNA's may be generated depending upon which acceptor splice site is used within the E6 region of the genome. The HPV type 16 genome appears to express all three types of E6 mRNA while the HPV type 18 genome appears to express HPV type 18 E6 and E6* only.

In a particular embodiment of this invention primers and probes have been designed to amplify and detect each one of the heterogeneous E6 messenger RNA species. In a more preferred embodiment, two types of E6 messenger RNA may be amplified and detected by a set of primers and probes in the same reaction vessel. In the most preferred embodiment, all E6 messenger RNA species of a particular type may be simultaneously amplified and detected in the same reaction vessel by the primers and probes of this invention.

EXAMPLES

Described herein are preferred sequences for hybridization assay probes, helper probes, and amplification oligonucleotides designed to hybridize to target sequences in HPV Type 16 and/or Type 18 RNA or DNA. In addition, preferred embodiments of mixes of hybridization assay probes and helper probes useful for detecting HPV Type 16 and/or Type 18 are described. Also described are hybrids formed by a hybridization assay probe and a target sequence. Preferred methods for using the probes and amplification oligonucleotides to detect HPV Type 16 and/or Type 18 are included in this description.

The following examples illustrate several preferred embodiments of the present invention and should in no way be considered as limiting the scope of the invention which is defined in the appended claims. Various modifications of these examples could readily be performed by those skilled in the art without departing from the scope of the invention as defined in the claims.

Example 1

Probes Distinguishing HPV Type 16 from Type 18 and Vice Versa

This example illustrates the specificity of probes designed to be specific for HPV type 16 and 18. One hundred million copies of plasmid DNA containing a portion of the E6 gene from either HPV type 16 or type 18 were hybridized to a probe of SEQ ID NO. 5 or SEQ ID NO. 45.

To perform the hybridization, linearized plasmid contained HPV DNA sequences were heated to 95° C. for 5 minutes in 50 µl of a solution containing $H_2O$ and cooled 1-2 minutes in a room temperature water bath. Then, 0.025-0.05 pmol ($\cong 2.6 \times 10^6$ RLUs/assay) of either (SEQ ID NO. 5) probe or SEQ ID NO. 45 probe was added to a final volume of 100 µl of 0.05 M lithium succinate pH 5, 0.6 M LiCl, 1% (w/v) lithium lauryl sulfate, 10 mM EDTA, 10 mM EGTA.

Hybridization was conducted at 60° C. for 15 minutes. Following hybridiziation, 300 µl of 0.15 M sodium tetraborate pH 8.5, 1% TRITON X-100 at 60° C. was added for 5 minutes. Samples were subsequently read in a luminometer equipped with automatic injection of 0.1% hydrogen peroxide in 1 mM nitric acid, followed by injection of a 1 N sodium hydroxide solution. The results, given in Table 1, are reported in Relative Light Units (RLU), a measure of the photons detected by the luminometer from labeled hybrids formed between probes SEQ ID NO. 5 and SEQ ID NO. 45 and their target nucleotide sequence.

TABLE 1

SPECIFICITY OF PROBES SEQ ID NOs. 5 & 45 FOR HPV TYPE 16 AND 18.

| | PROBE | |
|---|---|---|
| TARGET | SEQ ID NO. 5 RLU | SEQ ID NO. 45 RLU |
| HPV type 16 E6 cloned DNA | 226,896 | 1,048 |
| HPV type 18 E6 cloned DNA | 745 | 817,751 |

The results (an average of two trial hybridization reactions) demonstrate that probe SEQ ID NO. 5 detects HPV type 16 E6 sequences in preference to those of HPV type 18. Similarly, the probe SEQ ID NO. 45 detects HPV type 18 E6 sequences in preference to those of HPV type 16.

This example illustrates that the designed oligonucleotides are capable of distinguishing target sequences from phylogenetically close species, since HPV type 16 and HPV type 18 are immediately related phylogenetically (see, Van Ranst et al., *J. Gen. Vir.*, 73: 2653-60, 1992).

Example 2

Amplification and Detection of HPV Type 16 E6 DNA and RNA

This example illustrates the use of amplification oligonucleotides and hybridization assay probes targeted to HPV type 16 to facilitate amplification and detection of HPV type 16 nucleic acid. In this example, an assay probe for HPV type 16, of the same sense as E6 mRNA, was used to detect the products of a nucleic acid amplification method. (Kacian et al., supra).

Cloned DNA representing a portion of HPV type 16 E6 DNA was purified using a standard mini-prep procedure with reagents purchased from Qiagen®. Nucleic acid from cultured SiHa cells was prepared following trypsinization and centrifugation. The cell pellet was washed, resuspended and counted in phosphate buffered saline. Defined numbers of cells were pelleted and resuspended in Reagent I, a solution containing 3% (w/v) lithium lauryl sulfate, 30 mM sodium phosphate pH 6.8, 1.0 mM ethylene diamine tetra-acetic acid (EDTA), 1.0 mM ethylene glycol bis(beta-amino ethyl ether)

N, N, N', N' tetra-acetic acid (EGTA). Detergent was removed from samples by precipitation following addition of potassium acetate to a final concentration of 0.6 M. The nucleic acid contained in the supernatant was amplified directly.

The target nucleic acid was heated to 95° C. for 5 minutes, cooled to 60° C. for 15 minutes in 90 µl of a solution containing 30 pmole of a promoter-primer synthesized with a promoter sequence 5'-AATTTAATACGACTCACTATAGG-GAGA-3' (SEQ ID NO. 97) at the 5' end and a target hybridizing region 5'-CAGGACACAGTGGCTTTTGAC-3' at the 3' end (SEQ ID NO. 85), and 30 pmole of a primer synthesized with the sequence 5'-GACATTATTGTTAT-AGTTTGTATGGAAC-3' (SEQ ID NO. 1). Following a 5 minute incubation at 37° C., 900 U Moloney Murine Leukemia Virus (MMLV) reverse transcriptase and 400 U T7 RNA polymerase were added. The reactions were performed in 50 mM Tris-HCl, pH 7.6, 100 mM potassium acetate, 17.5 mM $MgCl_2$, 5.0 mM DTT, 2.0 mM spermidine, 6.2 mM rATP, 2.5 mM rCTP, 6.2 mM rGTP, 2.5 mM rUTP, 1 mM dATP, 1 mM dCTP, 1 mM dGTP, 1 mM dTTP, 7 mM N-Acetyl-L-cysteine, 0.03 mM EDTA, 3% glycerol, and 10% Tween.

Following a three hour incubation at 37° C., 10 µl of each reaction was assayed by hybridization using an acridinium ester labeled probe synthesized with sequence 5'-GAACAG-CAAT ACAACAAACC GTTGTGTG-3'(SEQ ID NO. 5) in 100 µl of 0.05 M lithium succinate pH 5, 0.6 M LiCl, 1% (w/v) lithium lauryl sulfate, 10 mM EDTA, 10 mM EGTA at 60° C. for 15 minutes, followed by addition of 300 µl of 0.15 M sodium tetraborate pH 8.5, 1% TRITON X-100 at 60° C. for 5 minutes.

Samples were read in a luminometer equipped with automatic injection of 0.1% hydrogen peroxide in 1 mM nitric acid, followed by injection of a 1 N sodium hydroxide solution. Results are given in Relative Light Units (RLU), a measure of the photons detected by the luminometer. The results shown are the average of two reactions.

TABLE 2

AMPLIFICATION AND DETECTION OF
HPV type 16 E6 DNA AND RNA.
HPV type 16 E6 nucleic acid

| copies cloned DNA | RLU |
|---|---|
| 0 | 945 |
| 1,000 | 5,247 |
| 10,000 | 35,620 |
| 1,000,000 | 881,886 |
| No. SiHa cells | |
| 100 | 1,335 |
| 1,000 | 2,182 |
| 10,000 | 428,602 |

These primers and probes were also able to amplify and detect DNA and RNA prepared from CaSki cells.

Example 3

Amplification and Detection of HPV Type 18 Sequences in HeLa Cell Extracts

This example illustrates the use of amplification oligonucleotides and hybridization assay probes targeted to HPV type 18 to amplify and detect HPV type 18 nucleic acid. In this example, an assay probe designed to HPV type 18, of the same sense as E6 mRNA, was used to detect the products of target nucleic acid amplification.

Cloned DNA representing a portion of the HPV type 18 E6 DNA, or nucleic acid prepared from HeLa cells (which contain HPV type 18 E6 nucleic acid sequences), was amplified with a primer synthesized with SEQ ID NO. 53 and a promoter primer containing the sequence (SEQ ID NO. 97) 5'-AATTTAATACGACTCACTATAGGGAGA-3' at the 5' end and a target hybridizing sequence (SEQ ID NO. 109) at the 3' end.

Cultured HeLa cells were trypsinized and centrifuged, washed, resuspended and counted in phosphate buffered saline. Defined numbers of cells were pelleted and suspended in Reagent I. The detergent was precipitated with a 0.6 M final concentration of potassium acetate and the nucleic acid contained in the supernatant was amplified directly. Cloned DNA was placed into a mock specimen prepared by potassium acetate precipitation of detergent from Reagent I.

The target nucleic acid was heated to 95° C. for 5 minutes, cooled to 60° C. for 15 minutes, then cooled to 37° C. in 90 µl of a solution containing 30 pmole each of the primer and promoter-primer. Following 5 minutes at 37° C., 900 U MMLV reverse transcriptase and 400 U T7 RNA polymerase were added. The reaction conditions were as described in Example 1.

Following a three hour incubation at 37° C., 10 µl of the reaction were assayed by hybridization using an acridinium ester labeled probe synthesized with SEQ ID NO. 45 in 100 µl of 0.05 M lithium succinate pH 5, 0.6 M LiCl, 1% (w/v) lithium lauryl sulfate, 10 mM EDTA, 10 mM EGTA at 55° C. for 15 minutes, followed by addition of 300 µl of 0.15 M sodium tetraborate pH 8.5, 1% TRITON X-100 and incubation at 55° C. for 5 minutes. Luminescence values of the samples were determined as described in Example 1.

TABLE 3

AMPLIFICATION AND DETECTION OF HPV TYPE
18 SEQUENCES IN HELA CELL EXTRACTS.*

| Copies cloned HPV type 18 E6 DNA | RLU |
|---|---|
| 0 | 862 |
| 100 | 15,993 |
| 1,000 | 279,565 |
| 10,000 | 820,591 |
| No. HeLa Cells | |
| 10,000 | 1,216,105 |
| 1,000 | 380,040 |
| 100 | 40,085 |

*Plasmid DNA was added following detergent precipitation. One HeLa cell contains approximately 10-50 copies of DNA. Therefore, 100 cells HeLa are equivalent to approximately 1,000-5,000 copies of DNA. HeLa number values which are lower than predicted from cloned DNA, are most likely the result of a loss of material during detergent precipitation.

Example 4

Amplification and Detection of Both HPV Type 16 and Type 18 in the Same Reaction Vessel Amplification oligonucleotides, as described herein, were designed to amplify both HPV type 16 and 18 DNA in the same reaction vessel, followed by detection with specific probes which can distinguish between the 16 and 18 variants. In this example, cloned target DNA from both HPV type 16 and 18 was amplified, followed by detection with the assay probes described.

Cloned DNA representing the HPV type 16 E6 DNA was amplified with a non-T7 primer consisting of SEQ ID NO. 1 and a promoter primer synthesized with a 3' target hybridizing sequence, SEQ ID NO. 85. Cloned DNA representing HPV type 18 DNA was amplified with a primer consisting of SEQ ID NO. 53 and a promoter primer with a 3' target hybridizing sequence SEQ ID NO. 109, both promoter primers containing the sequence 5'-AATTTAATACGACTCACTATAGG-GAGA-3' at their 5' end.

The target nucleic acid in detergent precipitated Reagent I was heated to 95° C. for 5 minutes, cooled to 60° C. for 15 minutes, then cooled to 37° C. in 90 µl of a solution containing 30 picomoles of each primer and promoter primer. Following 5 minutes at 37° C., 900 U MMLV reverse transcriptase and 400 U T7 RNA polymerase were added. The reaction conditions are as described in Example 1.

Following a three hour incubation at 37° C., ten µl of the reaction was assayed by hybridization using an acridinium ester labeled probe synthesized SEQ ID NO. 45, in 100 µl of 0.05 M lithium succinate pH 5, 0.6 M LiCl, 1% (w/v) lithium lauryl sulfate, 10 mM EDTA, 10 mM EGTA at 55° C. for 15 minutes, followed by addition of 300 µl of 0.15 M sodium tetraborate pH 8.5, 1% TRITON X-100 and incubation at 55° C. for 5 minutes. Ten µl of each reaction was also analyzed with acridinium ester labeled probe SEQ ID NO. 5 in 100 µl as described for probe SEQ ID NO. 45 except that the incubations were performed at 60° C. Luminescence values of samples were determined as described in Example 1.

As can be determined from Table 4, the designed oligonucleotide primers work well in the same reaction vessel. The amplification of either HPV Type 16 and/or Type 18 does not hinder amplification of the other Papillomavirus and the presence of either HPV Type 16 and/or Type 18 hybridization probe does not interfere with the ability of the other probe to distinguish HPV type 16 from 18 or vice versa. In fact, the specificity of each probe is ten times greater for its target than for a non-target nucleotide sequence.

TABLE 4

CO-AMPLIFICATION OF HPV TYPE 16 AND 18.

| PROBE | | RLU | |
|---|---|---|---|
| Copies HPV type 16 DNA | Copies HPV type 18 DNA | SEQ ID NO. 5 | SEQ ID NO. 45 |
| 1,000,000 | 1,000,000 | 1,115,026 | 1,057,903 |
| 10,000 | 1,000,000 | 643,415 | 974,109 |
| 1,000 | 1,000,000 | 152,810 | 944,290 |
| 100 | 1,000,000 | 6,852 | 930,188 |
| 0 | 0 | 1,243 | 1,140 |
| 1,000,000 | 1,000,000 | 991,682 | 886,852 |
| 1,000,000 | 10,000 | 1,003,151 | 821,532 |
| 1,000,000 | 1,000 | 1,001,966 | 389,796 |
| 1,000,000 | 100 | 997,714 | 10,157 |

Example 5

Designed Mismatch Primer can Amplify HPV Type 16 and/or Type 18 Separately or Simultaneously A promoter primer (SEQ ID NO. 113) was designed with mismatches to both HPV type 16 and 18 target nucleotide sequences. This promoter primer design has the ability to amplify both HPV type 16 and 18 DNA target sequences separately, or concurrently in the same reaction vessel.

Double stranded cloned targets were amplified with 30 pmole each of promoter primer synthesized with promoter SEQ ID NO. 97 at the 5' end and a target hybridizing SEQ ID NO. 113 or SEQ ID NO. 93 at the 3' end, in the presence of a primer synthesized with SEQ ID NO. 69 for HPV type 18 or a primer synthesized with SEQ ID NO. 37 for HPV type 16.

A 75 µl volume of the target nucleic acid was heated to 95° C. for 15 minutes and cooled to 42° C. Following 5 minutes at 42° C., 600 U MMLV reverse transcriptase and 300 U T7 RNA polymerase were added. Amplification reactions were performed in 50 mM Tris-HCl, pH 8.5, 5 mM potassium chloride, 20 mM MgCl$_2$, 4 mM rATP, 4 mM rCTP, 4 mM rGTP, 4 mM rUTP, 1 mM dATP, 1 mM dCTP, 1 mM dGTP, 1 mM dTTP, 20 mM N-Acetyl-L-cysteine, and 5% glycerol.

Following a two hour incubation at 42° C., triplicate amplification reactions were pooled and 100 µl of each pool was hybridized with an acridinium ester labeled probe synthesized with SEQ ID NO. 73 for the detection of HPV type 18 or SEQ ID NO. 33 for the detection of HPV type 16.

TABLE 5

CO-AMPLIFICATION OF HPV TYPE 16 AND 18 USING A MISMATCH PROMOTER PRIMER.

| | RLU Primers: | | |
|---|---|---|---|
| | SEQ ID NO No. 93/37 T7/Non-T7 | SEQ ID No. 113/69 T7/Non-T7 | SEQ ID Nos. 113/37 or 69 T7/Non-T7 |
| Probe: | SEQ ID No. 33 | SEQ ID No. 73 | SEQ ID Nos. 33 and 73 |
| Target | | | |
| 1,000 copies HPV type 16 DNA | 251,581 | 6,495 | 158,771 |
| 1,000 copies HPV type 18 DNA | 2,335 | 255,227 | 528,971 |
| 0 copies | 4,509 | 3,379 | 6,105 |

As can be seen from an examination of Table 5, the single mismatch promoter primer of SEQ ID NO. 113, can amplify two HPV nucleic acids (16 & 18) differing in sequence by 3 bases in the primer binding site.

Example 6

Amplification and Detection of Spliced E6* mRNA of HPV Type 16

This example illustrates the use of amplification oligonucleotides and hybridization assay probes for HPV type 16 to amplify and specifically detect E6* mRNA of HPV type 16. In this example, an assay probe of the same sense as the target E6* RNA nucleic acid was used to detect the products of a target nucleic acid amplification method.

Cultured SiHa cells were trypsinized, centrifuged, washed, resuspended and counted in phosphate buffered saline. Defined numbers of cells were pelleted and resuspended in Reagent I (i.e., Example 1). Detergent was removed from samples suspended in Reagent I by precipitation following addition of potassium acetate to a final concentration of 0.6 M. The nucleic acid contained in the supernatant was amplified directly.

The target nucleic acid was heated to 95° C. for 5 minutes, cooled to 60° C. for 15 minutes in 90 µl of a solution containing 30 pmole of each of the two primers. The promoter-primer had a target hybridizing region at the 3' end (SEQ ID NO. 89), and the second primer had a target hybridizing region (SEQ ID NO. 21) at its 3' end. Following 5 minutes at 37° C., 900 U MMLV reverse transcriptase and 400 U T7 RNA polymerase were added. The reaction conditions were as described in Example 1. [performed in 50 mM Tris-HCl, pH 7.6, 100 mM potassium acetate, 17.5 mM $MgCl_2$, 5.0 mM DTT, 2.0 mM spermidine, 6.2 mM rATP, 2.5 mM rCTP, 6.2 mM rGTP, 2.5 mM rUTP, 1 mM dATP, 1 mM dCTP, 1 mM dGTP, 1 mM dTTP, 7 mM N-Acetyl-L-cysteine, 0.03 mM EDTA, 3% glycerol, Tween-20®]. Following a three hour incubation at 37° C., 10 µl of the reaction was assayed by hybridization using an acridinium ester labeled probe synthesized with SEQ ID NO. 9 in 100 µl of 0.05 M lithium succinate pH 5, 0.6 M LiCl, 1% (w/v) lithium lauryl sulfate, 10 mM EDTA, 10 mM EGTA at 60° C. for 15 minutes, followed by addition of 300 µl of 0.15 M sodium tetraborate pH 8.5, 1% TRITON X-100 and incubation at 60° C. for 5 minutes. Luminescence values of the samples were determined as described in Example 1. The results are the average of two reactions.

TABLE 6

AMPLIFICATION AND DETECTION
OF HPV TYPE 16 E6* mRNA.

| No. SiHa cells | RLU |
|---|---|
| 0 | 656 |
| 1,000 | 18,391 |
| 10,000 | 418,717 |

These primers and probes were also able to amplify and detect DNA and RNA prepared from CaSki cells.

Example 7

Hybridization Assay Probes Detect HPV Type 16 E6, E6* and E6** Nucleic Acid

Assay probes designed for HPV type 16 are able to detect products of the amplification of E6 nucleic acid, including un-spliced, E6, E6* and E6** mRNA targets. The primer and promoter primer were oriented in such a way that the predominant amplification product was the same sense as the messenger RNA. In this example, nucleic acid prepared from Caski cells was used. Defined numbers of cells were pelleted and suspended in Reagent I. Potassium acetate was added to a final concentration of 0.6 M to precipitate the detergent and the nucleic acid contained in the supernatant was amplified directly. Nucleic acid from $1.6 \times 10^4$ cells was amplified as described in Example 1 with a promoter primer synthesized with a 5' T7 promoter and a 3' target hybridizing SEQ ID NO. 21, and 30 pmole of a primer synthesized with SEQ ID NO. 13. Ten µl of each reaction was hybridized to probes synthesized with SEQ ID NO. 29, SEQ ID NO. 25, or SEQ ID NO. 17.

TABLE 7

SPECIFIC DETECTION OF UN-SPLICED AND SPLICED
E6 MRNA PREPARED FROM CASKI CELLS.

| | RLU | | |
|---|---|---|---|
| Target: HPV16 | E6 mRNA | E6* mRNA | E6** mRNA |
| Probe: | SEQ ID NO. 29 | SEQ ID NO. 25 | SEQ ID NO. 17 |
| Sample | | | |
| 16,000 cells | 551,715 | 38,908 | 236,324 |
| 0 cells | 1,006 | 1,295 | 2,375 |

The results indicated in Table 7 support reports in the literature that the heterogeneous splice variations of E6 mRNA vary in quantity within the cell.

Example 8

Primers and Probes Detect HPV Type 18 E6* mRNA

Primers and probes capable of detecting the E6* mRN an HPV type 18 were designed. Defined numbers of HeLa cells were suspended in Reagent I and the nucleic acid was recovered following detergent precipitation, as in Example 7, and amplified directly. Amplification reactions were performed with a promoter primer synthesized with a 5' promoter SEQ ID NO. 97 and a target hybridizing region SEQ ID NO. 101, and a primer consisting of SEQ ID NO. 49. Reaction conditions were as in Example 1. Ten µl of the amplification reaction was hybridized with an acridinium ester labeled probe synthesized with SEQ ID NO. 77 in 100 µl of 0.05 M lithium succinate pH 5, 0.6 M LiCl, 1% (w/v) lithium lauryl sulfate, 10 mM EDTA, 10 mM EGTA at 55° C. for 15 minutes, followed by addition of 300 µl of 0.15 M sodium tetraborate pH 8.5, 1% TRITON X-100 at 55° C. for 5 minutes. Luminescence values were determined as in Example 1.

TABLE 8

AMPLIFICATION AND DETECTION OF HPV TYPE 18 E6* mRNA
HPV type 18 E6*

| No. HeLa cells | RLU |
|---|---|
| 10,000 | 1,309,947 |
| 1,000 | 18,231 |
| 100 | 2,750 |
| 0 | 1,144 |

Example 9

Probes & Primers Amplify & Detect Both Spliced and Unspliced HPV Type 18 E6 mRNA Primers and probes were designed to amplify and detect un-spliced and spliced E6 sequences of HPV type 18. A primer synthesized with SEQ ID NO. 41 and a promoter primer synthesized with a 5' promoter sequence (SEQ ID NO. 97) 5'-AATTTAATACGACTCACTATAGGGAGA-3' and a 3' target hybridizing region SEQ ID NO. 109 were used to amplify cloned DNA representing HPV type 18 E6 sequences. The target nucleic acid was heated to 95° C. for 15 minutes, and cooled to 42° C. in 75 µl of a solution containing 25 picomoles of the primer and promoter primer. Following 5 minutes at 42° C., 600 U MMLV reverse transcriptase and 300 U T7 RNA polymerase were added. Amplification reactions were performed in 50 mM Tris-HCl, pH 8.5, 35 mM potassium acetate, 20 mM $MgCl_2$, 4 mM rATP, 4 mM rCTP, 4 mM rGTP, 4 mM rUTP, 1 mM dATP, 1 mM dCTP, 1 mM dGTP, 1 mM dTTP, 20 mM N-Acetyl-L-cysteine, and 5% glycerol. Following a two hour incubation at 42° C., 20 µl of each reaction was assayed by hybridization using an acridinium ester labeled probe of SEQ ID NO. 81 for E6* detection, SEQ ID NO. 65 for E6 detection, or SEQ ID NO. 57 for both E6 and E6* detection, using conditions described in Example 1. An unlabeled helper probe consisting of sequence SEQ ID NO. 61 was used with probes 81 and 65, an unlabeled helper probe of sequence SEQ ID NO. 117 was used with probe SEQ ID NO. 57.

TABLE 9

AMPLIFICATION AND DETECTION OF HPV TYPE
18 SPLICED AND UNSPLICED E6 mRNA

| | RLU | | |
|---|---|---|---|
| Target: HPV18 | E6* | E6 | E6 and E6* |
| Probe: | SEQ ID NO. 81 | SEQ ID NO. 65 | SEQ ID NO. 57 |
| Helper: | SEQ ID NO. 61 | SEQ ID NO. 61 | SEQ ID NO. 117 |
| E6 Target added to reaction: | | | |
| $10^6$ unspliced | 1,057 | 912,867 | 975,288 |
| $10^5$ unspliced | 703 | 343,900 | 406,958 |
| $10^4$ unspliced | 546 | 208,246 | 255,093 |
| $10^3$ unspliced | 582 | 58,946 | 90,836 |
| $10^6$ spliced | 1,387,098 | 5,709 | 1,499,335 |
| $10^5$ spliced | 704,412 | 3,430 | 807,331 |
| $10^4$ spliced | 184,847 | 1,446 | 300,340 |
| $10^3$ spliced | 27,907 | 936 | 46,798 |
| Negative | 564 | 1,542 | 619 |

Example 10

HPV Type 16 & 18 Detection from Clinical Samples

Endocervial swabs from patients attending a clinic were placed into a tube containing 5 ml of Reagent I. The swabs were expressed and discarded. Nucleic acid from Reagent I was extracted following addition of potassium acetate to 0.6 M and removal of the detergent pellet by centrifugation. A sample of the nucleic acid in the supernatant was analyzed for the presence of HPV by established procedures. In one test, a portion of the nucleic acid was phenol chloroform extracted and amplified by polymerase chain reaction using published primers targeting the L1 gene sequences. Samples were also assayed for amplification of L1 sequences by agarose gel analysis directly or following restriction endonuclease digestion. Alternatively, samples were analyzed by hybridization with acridinium ester labeled probes directed to published sequences of HPV type 16 and 18. Samples positive by gel for types other than HPV type 16 or HPV type 18 were assayed by with acridinium ester labeled L1 probes corresponding to the identified type (HPV 6, 11, 31, 33, 35, 39, 45, 51, 52 and 58) for confirmation. Samples characterized in this manner were then tested in the amplification format using the primers and promoter primers described herein. Amplified samples were assayed by HPA with detection probes directed to HPV type 16 (SEQ ID NO. 5) or HPV type 18 (SEQ ID NO. 45) sequences.

TABLE 10

DETECTION OF HPV TYPE 16 &
18 FROM CLINICAL SAMPLES

| Clinical isolate number | HPV type by L1 PCR RFLP | HPV type by AE probe hybridization | Amplification result |
|---|---|---|---|
| 16 | 6 | 6 | 16− |
| 25 | 6 | 6 | 16− |
| 28 | 6 | 6 | 16− |
| 797 | 6 | 6 + 11 + 33 | 16− |
| 3 | 16 | 16 | 16+ |
| 29 | 16 | 16 | 16+ |
| 41 | 16 | 16 | 16+ |
| 72 | 16 + 6 | 16 + 6 | 16+ |
| 133 | 16 | 16 | 16+ |
| 146 | 16 | 16 | 16+ |
| 173 | 16 + 33 | 16 + 33 | 16+ |
| 185 | 16 + Gx3(*) | 16 | 16+ |
| 190 | 16 | 16 | 16+ |
| 204 | 16 | 16 | 16+ |
| 216 | 16 | 16 | 16+ |
| 224 | 16 + Gx3(*) | 16 | 16+ |
| 234 | 16 | 16 | 16+ |
| 293 | 16 + 35 | 16 + 35 | 16+ |
| 341 | 16 | 16 | 16+ |
| 364 | 16 | 16 | 16+ |
| 368 | 16 + 58 | 16 | 16+ |
| 369 | 16 + 58 | 16 | 16+ |
| 370 | 16 + 58 | 16 | 16+ |
| 789 | 16 | 16 | 16+ |
| 796 | 16 | 16 | 16+ |
| 96 | 18 | 18 | 18+ |
| 114 | 18 | 18 | 18+ |
| 177 | 18 + Gx9(*) | 18 | 16−<br>18+ |
| 290 | 18 | 18 + 16 | 18 |
| 297 | 18 | 18 | 18 |
| 798 | 11 + 18 | 18 | 18 |
| 101 | 31 | 31 | 16− |
| 118 | 31 | 31 | 16− |
| 115 | 33 | 33 | 16− |
| 166 | 33 | 33 | 16− |
| 791 | 33 | 33 | 16− |
| 192 | 39 | N.D. | 16− |
| 109 | 58 | N.D. | 16− |
| 175 | 58 | N.D. | 16− |
| 176 | 58 | N.D. | 16− |
| 182 | 58 | N.D. | 16− |
| 779 | 58 | N.D. | 16− |

The data in this table are reported as positive if the RLU value was over the value of the negative control by a factor of 1.5-2.0× for the luminometer employed in this example. Acridinium ester labeled probe SEQ ID NO. 5 was used for detection of HPV type 16 and acridinium labeled probe SEQ ID NO. 45 was used with unlabeled helper probe SEQ ID NOs. 121, 123, 127, or 125 for detection of HPV type 18.

The data shown in the various examples described above confirm that the novel probes herein described and claimed are capable of distinguishing HPV from their known nearest phylogenetic neighbors. Furthermore, complementary oligonucleotide probes, i.e., those having the same sense as the target, are utilized to detect the products of target amplification procedures now being utilized to increase the detection sensitivity of assays for organisms.

Sequence information was obtained experimentally and from published information. (See Weisburg, et al., *J. Bacteriol* 171:6455 (1989).) Experimental information was obtained by isolating and sequencing RNA or DNA from various organisms using standard techniques known in the art. More specifically, RNA sequence information was obtained by first using oligonucleotide primers complementary to conserved regions which vary little between prokaryotic organisms. The oligonucleotide primers were hybridized to the conserved regions in purified RNA and extended with the enzyme reverse transcriptase and deoxyribonucleotides to produce cDNA. E.g., Lane et al., *Proc. Nat'l Acad. Sci. USA* 82:6955 (1985).

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Those references not previously incorporated herein by reference, including both patent and non-patent references, are expressly incorporated herein by reference for all purposes. Other embodiments are within the following claims.

We claim:

1. A method of detecting a HPV Type 16 nucleic acid in a sample comprising the steps of:
   a) contacting an HPV type 16 amplification product with at least one hybridization assay detection probe that forms a detectable probe: HPV type 16 target hybrid under stringent hybridization conditions, wherein the at least one hybridization assay detection probe comprises a detectable label joined to a contiguous nucleic acid sequence that is from 21 to 27 nucleotides in length, (a) contained within a sequence consisting of SEQ ID NO:13 or an RNA equivalent thereof, and contains a sequence consisting of SEQ ID NO:34 or an RNA equivalent thereof, or (b) contained within a sequence consisting of SEQ ID NO:14 or an RNA equivalent thereof, and contains a sequence consisting of SEQ ID NO:33 or an RNA equivalent thereof; and
   b) detecting a signal from the probe: HPV type 16 target hybrid, thereby indicating the presence of HPV type 16 in the sample.

2. The method of claim 1, wherein the contiguous nucleic acid sequence comprises a sequence selected from the group consisting of: SEQ ID NO:13; SEQ ID NO:14; SEQ ID NO:15; and SEQ ID NO:16.

3. The method of claim 1, wherein the contiguous nucleic acid sequence comprises a sequence selected from the group consisting of: SEQ ID NO:33; SEQ ID NO:34; SEQ ID NO:35; and SEQ ID NO:36.

4. The method of claim 1, wherein at least one of the nucleotide residues in the contiguous nucleic acid sequence of the probe is a 2'Omethyl ribose.

5. The method of claim 1, wherein a fluorescent detectable label is joined to the contiguous nucleic acid sequence.

6. The method of claim 1, wherein a chemiluminescent detectable label is joined to the contiguous nucleic acid sequence.

7. The method of claim 6, further comprising a helper probe.

8. The method of claim 1, further comprising a helper probe.

9. The method of claim 1, wherein the hybridization assay detection probe comprises at least one chemiluminescent detectable label joined to the contiguous nucleic acid sequence wherein at least one of the residues of the contiguous nucleic acid sequence is a 2'Omethyl ribose, and wherein the contiguous nucleic acid sequence is selected from the group consisting of: (i) a nucleic acid sequence that is from 21 to 27 nucleotides in length, is contained within a sequence consisting of an RNA equivalent of SEQ ID NO:13 and contains an RNA equivalent of SEQ ID NO:34; and (ii) a nucleic acid sequence that is 21 to 27 nucleotides in length, is contained within a sequence consisting of and RNA equivalent of SEQ ID NO:14 and contains an RNA equivalent of SEQ ID NO:33.

10. The method of claim 1, wherein the sample is a clinical sample.

11. The method of claim 1, wherein the hybridization assay detection probe forms a detectable probe: HPV type 16 target hybrid under selective stringency hybridization conditions.

12. The method of claim 1, wherein the sample type is selected from the group consisting of: urine samples, tissue sections, urogenital secretions, and urogenital swabs.

* * * * *

SEQUENCE LISTING

```
<160> NUMBER OF SEQ ID NOS: 128

<210> SEQ ID NO 1
<211> LENGTH: 28
<212> TYPE: DNA
<213> ORGANISM: Artificial
<220> FEATURE:
<223> OTHER INFORMATION: Synthetic oligonucleotide

<400> SEQUENCE: 1
gacattattg ttatagtttg tatggaac                                        28

<210> SEQ ID NO 2
<211> LENGTH: 28
<212> TYPE: DNA
<213> ORGANISM: Artificial
<220> FEATURE:
<223> OTHER INFORMATION: Synthetic oligonucleotide

<400> SEQUENCE: 2
gttccataca aactataaca ataatgtc                                        28

<210> SEQ ID NO 3
<211> LENGTH: 28
<212> TYPE: RNA
<213> ORGANISM: Artificial
<220> FEATURE:
<223> OTHER INFORMATION: Synthetic oligonucleotide

<400> SEQUENCE: 3
gacauuauug uuauaguuug uauggaac                                        28

<210> SEQ ID NO 4
<211> LENGTH: 28
<212> TYPE: RNA
<213> ORGANISM: Artificial
<220> FEATURE:
<223> OTHER INFORMATION: Synthetic oligonucleotide

<400> SEQUENCE: 4
guuccauaca aacuauaaca auaauguc                                        28

<210> SEQ ID NO 5
<211> LENGTH: 28
<212> TYPE: DNA
<213> ORGANISM: Artificial
<220> FEATURE:
<223> OTHER INFORMATION: Synthetic oligonucleotide

<400> SEQUENCE: 5
gaacagcaat acaacaaacc gttgtgtg                                        28

<210> SEQ ID NO 6
<211> LENGTH: 28
<212> TYPE: DNA
<213> ORGANISM: Artificial
```

```
<220> FEATURE:
<223> OTHER INFORMATION: Synthetic Oligonucleotide

<400> SEQUENCE: 6
cacacaacgg tttgttgtat tgctgttc                                        28

<210> SEQ ID NO 7
<211> LENGTH: 28
<212> TYPE: RNA
<213> ORGANISM: Artificial
<220> FEATURE:
<223> OTHER INFORMATION: Synthetic oligonucleotide

<400> SEQUENCE: 7
gaacagcaau acaacaaacc guugugug                                        28

<210> SEQ ID NO 8
<211> LENGTH: 28
<212> TYPE: RNA
<213> ORGANISM: Artificial
<220> FEATURE:
<223> OTHER INFORMATION: Synthetic oligonucleotide

<400> SEQUENCE: 8
cacacaacgg uuuguuguau ugcuguuc                                        28

<210> SEQ ID NO 9
<211> LENGTH: 27
<212> TYPE: DNA
<213> ORGANISM: Artificial
<220> FEATURE:
<223> OTHER INFORMATION: Synthetic oligonucleotide

<400> SEQUENCE: 9
gacgtgaggt gtattaactg tcaaaag                                         27

<210> SEQ ID NO 10
<211> LENGTH: 27
<212> TYPE: DNA
<213> ORGANISM: Artificial
<220> FEATURE:
<223> OTHER INFORMATION: Synthetic oligonucleotide

<400> SEQUENCE: 10
cttttgacag ttaatacacc tcacgtc                                         27

<210> SEQ ID NO 11
<211> LENGTH: 27
<212> TYPE: RNA
<213> ORGANISM: Artificial
<220> FEATURE:
<223> OTHER INFORMATION: Synthetic oligonucleotide

<400> SEQUENCE: 11
gacgugaggu guauuacug ucaaaag                                          27

<210> SEQ ID NO 12
<211> LENGTH: 27
<212> TYPE: RNA
<213> ORGANISM: Artificial
<220> FEATURE:
<223> OTHER INFORMATION: Synthetic oligonucleotide

<400> SEQUENCE: 12
cuuuugacag uuaauacacc ucacguc                                         27
```

<210> SEQ ID NO 13
<211> LENGTH: 27
<212> TYPE: DNA
<213> ORGANISM: Artificial
<220> FEATURE:
<223> OTHER INFORMATION: Synthetic oligonucleotide

<400> SEQUENCE: 13
ccatgcatga ttacagctgg gtttctc                                        27

<210> SEQ ID NO 14
<211> LENGTH: 27
<212> TYPE: DNA
<213> ORGANISM: Artificial
<220> FEATURE:
<223> OTHER INFORMATION: Synthetic oligonucleotide

<400> SEQUENCE: 14
gagaaaccca gctgtaatca tgcatgg                                        27

<210> SEQ ID NO 15
<211> LENGTH: 27
<212> TYPE: RNA
<213> ORGANISM: Artificial
<220> FEATURE:
<223> OTHER INFORMATION: Synthetic oligonucleotide

<400> SEQUENCE: 15
ccaugcauga uuacagcugg guuucuc                                        27

<210> SEQ ID NO 16
<211> LENGTH: 27
<212> TYPE: RNA
<213> ORGANISM: Artificial
<220> FEATURE:
<223> OTHER INFORMATION: Synthetic oligonucleotide

<400> SEQUENCE: 16
gagaaaccca gcuguaauca ugcaugg                                        27

<210> SEQ ID NO 17
<211> LENGTH: 26
<212> TYPE: DNA
<213> ORGANISM: Artificial
<220> FEATURE:
<223> OTHER INFORMATION: Synthetic oligonucleotide

<400> SEQUENCE: 17
tacgtgttct tgatgatctc acgtcg                                         26

<210> SEQ ID NO 18
<211> LENGTH: 26
<212> TYPE: DNA
<213> ORGANISM: Artificial
<220> FEATURE:
<223> OTHER INFORMATION: Synthetic oligonucleotide

<400> SEQUENCE: 18
cgacgtgaga tcatcaagaa cacgta                                         26

<210> SEQ ID NO 19
<211> LENGTH: 26
<212> TYPE: RNA
<213> ORGANISM: Artificial
<220> FEATURE:
<223> OTHER INFORMATION: Synthetic oligonucleotide

```
<400> SEQUENCE: 19
uacguguucu ugaugaucuc acgucg                                              26

<210> SEQ ID NO 20
<211> LENGTH: 26
<212> TYPE: RNA
<213> ORGANISM: Artificial
<220> FEATURE:
<223> OTHER INFORMATION: Synthetic oligonucleotide

<400> SEQUENCE: 20
cgacgugaga ucaucaagaa cacgua                                              26

<210> SEQ ID NO 21
<211> LENGTH: 26
<212> TYPE: DNA
<213> ORGANISM: Artificial
<220> FEATURE:
<223> OTHER INFORMATION: Synthetic oligonucleotide

<400> SEQUENCE: 21
gtgtgtactg caagcaacag ttactg                                              26

<210> SEQ ID NO 22
<211> LENGTH: 26
<212> TYPE: DNA
<213> ORGANISM: Artificial
<220> FEATURE:
<223> OTHER INFORMATION: Synthetic oligonucleotide

<400> SEQUENCE: 22
cagtaactgt tgcttgcagt acacac                                              26

<210> SEQ ID NO 23
<211> LENGTH: 26
<212> TYPE: RNA
<213> ORGANISM: Artificial
<220> FEATURE:
<223> OTHER INFORMATION: Synthetic oligonucleotide

<400> SEQUENCE: 23
guguguacug caagcaacag uuacug                                              26

<210> SEQ ID NO 24
<211> LENGTH: 26
<212> TYPE: RNA
<213> ORGANISM: Artificial
<220> FEATURE:
<223> OTHER INFORMATION: Synthetic oligonucleotide

<400> SEQUENCE: 24
caguaacugu ugcuugcagu acacac                                              26

<210> SEQ ID NO 25
<211> LENGTH: 25
<212> TYPE: DNA
<213> ORGANISM: Artificial
<220> FEATURE:
<223> OTHER INFORMATION: Synthetic oligonucleotide

<400> SEQUENCE: 25
cttttgacag ttaatacacc tcacg                                               25

<210> SEQ ID NO 26
```

```
<211> LENGTH: 25
<212> TYPE: DNA
<213> ORGANISM: Artificial
<220> FEATURE:
<223> OTHER INFORMATION: Synthetic oligonucleotide

<400> SEQUENCE: 26
cgtgaggtgt attaactgtc aaaag                                              25

<210> SEQ ID NO 27
<211> LENGTH: 25
<212> TYPE: RNA
<213> ORGANISM: Artificial
<220> FEATURE:
<223> OTHER INFORMATION: Synthetic oligonucleotide

<400> SEQUENCE: 27
cuuuugacag uuaauacacc ucacg                                              25

<210> SEQ ID NO 28
<211> LENGTH: 25
<212> TYPE: RNA
<213> ORGANISM: Artificial
<220> FEATURE:
<223> OTHER INFORMATION: Synthetic oligonucleotide

<400> SEQUENCE: 28
cgugaggugu auuaacuguc aaaag                                              25

<210> SEQ ID NO 29
<211> LENGTH: 22
<212> TYPE: DNA
<213> ORGANISM: Artificial
<220> FEATURE:
<223> OTHER INFORMATION: Synthetic oligonucleotide

<400> SEQUENCE: 29
aaagtcatat acctcacgtc gc                                                 22

<210> SEQ ID NO 30
<211> LENGTH: 22
<212> TYPE: DNA
<213> ORGANISM: Artificial
<220> FEATURE:
<223> OTHER INFORMATION: Synthetic oligonucleotide

<400> SEQUENCE: 30
gcgacgtgag gtatatgact tt                                                 22

<210> SEQ ID NO 31
<211> LENGTH: 22
<212> TYPE: RNA
<213> ORGANISM: Artificial
<220> FEATURE:
<223> OTHER INFORMATION: Synthetic oligonucleotide

<400> SEQUENCE: 31
aaagucauau accucacguc gc                                                 22

<210> SEQ ID NO 32
<211> LENGTH: 22
<212> TYPE: RNA
<213> ORGANISM: Artificial
<220> FEATURE:
<223> OTHER INFORMATION: Synthetic oligonucleotide

<400> SEQUENCE: 32
```
gcgacgugag guauaugacu uu                                              22

<210> SEQ ID NO 33
<211> LENGTH: 21
<212> TYPE: DNA
<213> ORGANISM: Artificial
<220> FEATURE:
<223> OTHER INFORMATION: Synthetic oligonucleotide

<400> SEQUENCE: 33
gaaacccagc tgtaatcatg c                                               21

<210> SEQ ID NO 34
<211> LENGTH: 21
<212> TYPE: DNA
<213> ORGANISM: Artificial
<220> FEATURE:
<223> OTHER INFORMATION: Synthetic oligonucleotide

<400> SEQUENCE: 34
gcatgattac agctgggttt c                                               21

<210> SEQ ID NO 35
<211> LENGTH: 21
<212> TYPE: RNA
<213> ORGANISM: Artificial
<220> FEATURE:
<223> OTHER INFORMATION: Synthetic oligonucleotide

<400> SEQUENCE: 35
gaaacccagc uguaaucaug c                                               21

<210> SEQ ID NO 36
<211> LENGTH: 21
<212> TYPE: RNA
<213> ORGANISM: Artificial
<220> FEATURE:
<223> OTHER INFORMATION: Synthetic oligonucleotide

<400> SEQUENCE: 36
gcaugauuac agcuggguuu c                                               21

<210> SEQ ID NO 37
<211> LENGTH: 19
<212> TYPE: DNA
<213> ORGANISM: Artificial
<220> FEATURE:
<223> OTHER INFORMATION: Synthetic oligonucleotide

<400> SEQUENCE: 37
gatcatcaag aacacgtag                                                  19

<210> SEQ ID NO 38
<211> LENGTH: 19
<212> TYPE: DNA
<213> ORGANISM: Artificial
<220> FEATURE:
<223> OTHER INFORMATION: Synthetic oliognucleotide

<400> SEQUENCE: 38
ctacgtgttc ttgatgatc                                                  19

<210> SEQ ID NO 39
<211> LENGTH: 19
<212> TYPE: RNA

```
<213> ORGANISM: Artificial
<220> FEATURE:
<223> OTHER INFORMATION: Synthetic oligonucleotide

<400> SEQUENCE: 39
gaucaucaag aacacguag                                                    19

<210> SEQ ID NO 40
<211> LENGTH: 19
<212> TYPE: RNA
<213> ORGANISM: Artificial
<220> FEATURE:
<223> OTHER INFORMATION: Synthetic oligonucleotide

<400> SEQUENCE: 40
cuacguguuc uugaugauc                                                    19

<210> SEQ ID NO 41
<211> LENGTH: 37
<212> TYPE: DNA
<213> ORGANISM: Artificial
<220> FEATURE:
<223> OTHER INFORMATION: Synthetic oligonucleotide

<400> SEQUENCE: 41
ggaactgaac acttcactgc aagacataga aataacc                                37

<210> SEQ ID NO 42
<211> LENGTH: 37
<212> TYPE: DNA
<213> ORGANISM: Artificial
<220> FEATURE:
<223> OTHER INFORMATION: Synthetic oligonucleotide

<400> SEQUENCE: 42
ggttatttct atgtcttgca gtgaagtgtt cagttcc                                37

<210> SEQ ID NO 43
<211> LENGTH: 37
<212> TYPE: RNA
<213> ORGANISM: Artificial
<220> FEATURE:
<223> OTHER INFORMATION: Synthetic oligonucleotide

<400> SEQUENCE: 43
ggaacugaac acuucacugc aagacauaga aauaacc                                37

<210> SEQ ID NO 44
<211> LENGTH: 37
<212> TYPE: RNA
<213> ORGANISM: Artificial
<220> FEATURE:
<223> OTHER INFORMATION: Synthetic oligonucleotide

<400> SEQUENCE: 44
gguuauuucu augucuugca gugaaguguu caguucc                                37

<210> SEQ ID NO 45
<211> LENGTH: 31
<212> TYPE: DNA
<213> ORGANISM: Artificial
<220> FEATURE:
<223> OTHER INFORMATION: Synthetic oligonucleotide

<400> SEQUENCE: 45
ggaaaaacta actaacactg ggttatacaa t                                      31
```

<210> SEQ ID NO 46
<211> LENGTH: 31
<212> TYPE: DNA
<213> ORGANISM: Artificial
<220> FEATURE:
<223> OTHER INFORMATION: Synthetic oligonucleotide

<400> SEQUENCE: 46
attgtataac ccagtgttag ttagttttte c                                31

<210> SEQ ID NO 47
<211> LENGTH: 31
<212> TYPE: RNA
<213> ORGANISM: Artificial
<220> FEATURE:
<223> OTHER INFORMATION: Synthetic oligonucleotide

<400> SEQUENCE: 47
ggaaaaacua acuaacacug gguuauacca u                                31

<210> SEQ ID NO 48
<211> LENGTH: 31
<212> TYPE: RNA
<213> ORGANISM: Artificial
<220> FEATURE:
<223> OTHER INFORMATION: Synthetic oligonucleotide

<400> SEQUENCE: 48
auuguauaac ccaguguuag uuaguuuuuc c                                31

<210> SEQ ID NO 49
<211> LENGTH: 28
<212> TYPE: DNA
<213> ORGANISM: Artificial
<220> FEATURE:
<223> OTHER INFORMATION: Synthetic oligonucleotide

<400> SEQUENCE: 49
catagaaata acctgtgtat attgcaag                                    28

<210> SEQ ID NO 50
<211> LENGTH: 28
<212> TYPE: DNA
<213> ORGANISM: Artificial
<220> FEATURE:
<223> OTHER INFORMATION: Synthetic oligonucleotide

<400> SEQUENCE: 50
cttgcaatat acacaggtta tttctatg                                    28

<210> SEQ ID NO 51
<211> LENGTH: 28
<212> TYPE: RNA
<213> ORGANISM: Artificial
<220> FEATURE:
<223> OTHER INFORMATION: Synthetic oligonucleotide

<400> SEQUENCE: 51
cauagaaaua accuguguau auugcaag                                    28

<210> SEQ ID NO 52
<211> LENGTH: 28
<212> TYPE: RNA
<213> ORGANISM: Artificial
<220> FEATURE:

<223> OTHER INFORMATION: Synthetic oligonucleotide

<400> SEQUENCE: 52
cuugcaauau acacagguua uuucuaug                                           28

<210> SEQ ID NO 53
<211> LENGTH: 27
<212> TYPE: DNA
<213> ORGANISM: Artificial
<220> FEATURE:
<223> OTHER INFORMATION: Synthetic oligonucleotide

<400> SEQUENCE: 53
gacattattc agactctgtg tatggag                                            27

<210> SEQ ID NO 54
<211> LENGTH: 27
<212> TYPE: DNA
<213> ORGANISM: Artificial
<220> FEATURE:
<223> OTHER INFORMATION: Synthetic oligonucleotide

<400> SEQUENCE: 54
ctccatacac agagtctgaa taatgtc                                            27

<210> SEQ ID NO 55
<211> LENGTH: 27
<212> TYPE: RNA
<213> ORGANISM: Artificial
<220> FEATURE:
<223> OTHER INFORMATION: Synthetic oligonucleotide

<400> SEQUENCE: 55
gacauuauuc agacucugug uauggag                                            27

<210> SEQ ID NO 56
<211> LENGTH: 27
<212> TYPE: RNA
<213> ORGANISM: Artificial
<220> FEATURE:
<223> OTHER INFORMATION: Synthetic oligonucleotide

<400> SEQUENCE: 56
cuccauacac agagucugaa uaauguc                                            27

<210> SEQ ID NO 57
<211> LENGTH: 26
<212> TYPE: DNA
<213> ORGANISM: Artificial
<220> FEATURE:
<223> OTHER INFORMATION: Synthetic oligonucleotide

<400> SEQUENCE: 57
gcaagacagt attggaactt acagag                                             26

<210> SEQ ID NO 58
<211> LENGTH: 26
<212> TYPE: DNA
<213> ORGANISM: Artificial
<220> FEATURE:
<223> OTHER INFORMATION: Synthetic oligonucleotide

<400> SEQUENCE: 58
ctctgtaagt tccaatactg tcttgc                                             26

```
<210> SEQ ID NO 59
<211> LENGTH: 26
<212> TYPE: RNA
<213> ORGANISM: Artificial
<220> FEATURE:
<223> OTHER INFORMATION: Synthetic oligonucleotide

<400> SEQUENCE: 59
gcaagacagu auuggaacuu acagag                                              26

<210> SEQ ID NO 60
<211> LENGTH: 26
<212> TYPE: DNA
<213> ORGANISM: Artificial
<220> FEATURE:
<223> OTHER INFORMATION: Synthetic oligonucleotide

<400> SEQUENCE: 60
cuctguaagu uccaauacug ucuugc                                              26

<210> SEQ ID NO 61
<211> LENGTH: 26
<212> TYPE: DNA
<213> ORGANISM: Artificial
<220> FEATURE:
<223> OTHER INFORMATION: Synthetic oligonucleotide

<400> SEQUENCE: 61
cctgtgtata ttgcaagaca gtattg                                              26

<210> SEQ ID NO 62
<211> LENGTH: 26
<212> TYPE: DNA
<213> ORGANISM: Artificial
<220> FEATURE:
<223> OTHER INFORMATION: Synthetic oligonucleotide

<400> SEQUENCE: 62
caatactgtc ttgcaatata cacagg                                              26

<210> SEQ ID NO 63
<211> LENGTH: 26
<212> TYPE: RNA
<213> ORGANISM: Artificial
<220> FEATURE:
<223> OTHER INFORMATION: Synthetic oligonucleotide

<400> SEQUENCE: 63
ccuguguaua uugcaagaca guauug                                              26

<210> SEQ ID NO 64
<211> LENGTH: 26
<212> TYPE: RNA
<213> ORGANISM: Artificial
<220> FEATURE:
<223> OTHER INFORMATION: Synthetic oligonucleotide

<400> SEQUENCE: 64
caauacuguc uugcaauaua cacagg                                              26

<210> SEQ ID NO 65
<211> LENGTH: 26
<212> TYPE: DNA
<213> ORGANISM: Artificial
<220> FEATURE:
<223> OTHER INFORMATION: Synthetic oligonucleotide
```

```
<400> SEQUENCE: 65
gaacttacag aggtatttga atttgc                                              26

<210> SEQ ID NO 66
<211> LENGTH: 26
<212> TYPE: DNA
<213> ORGANISM: Artificial
<220> FEATURE:
<223> OTHER INFORMATION: Synthetic oligonucleotide

<400> SEQUENCE: 66
gcaaattcaa atacctctgt aagttc                                              26

<210> SEQ ID NO 67
<211> LENGTH: 26
<212> TYPE: RNA
<213> ORGANISM: Artificial
<220> FEATURE:
<223> OTHER INFORMATION: Synthetic oligonucleotide

<400> SEQUENCE: 67
gaacuuacag agguauuuga auuugc                                              26

<210> SEQ ID NO 68
<211> LENGTH: 26
<212> TYPE: RNA
<213> ORGANISM: Artificial
<220> FEATURE:
<223> OTHER INFORMATION: Synthetic oligonucleotide

<400> SEQUENCE: 68
gcaaauucaa auaccucugu aaguuc                                              26

<210> SEQ ID NO 69
<211> LENGTH: 23
<212> TYPE: DNA
<213> ORGANISM: Artificial
<220> FEATURE:
<223> OTHER INFORMATION: Synthetic oligonucleotide

<400> SEQUENCE: 69
caaccgagca cgacaggaac gac                                                 23

<210> SEQ ID NO 70
<211> LENGTH: 23
<212> TYPE: DNA
<213> ORGANISM: Artificial
<220> FEATURE:
<223> OTHER INFORMATION: Synthetic oligonucleotide

<400> SEQUENCE: 70
gtcgttcctg tcgtgctcgg ttg                                                 23

<210> SEQ ID NO 71
<211> LENGTH: 23
<212> TYPE: DNA
<213> ORGANISM: Artificial
<220> FEATURE:
<223> OTHER INFORMATION: Synthetic oligonucleotide

<400> SEQUENCE: 71
caaccgagca cgacaggaac gac                                                 23

<210> SEQ ID NO 72
<211> LENGTH: 23
```

```
<212> TYPE: RNA
<213> ORGANISM: Artificial
<220> FEATURE:
<223> OTHER INFORMATION: Synthetic oligonucleotide

<400> SEQUENCE: 72
gucguuccug ucgugcucgg uug                                           23

<210> SEQ ID NO 73
<211> LENGTH: 23
<212> TYPE: DNA
<213> ORGANISM: Artificial
<220> FEATURE:
<223> OTHER INFORMATION: Synthetic oligonucleotide

<400> SEQUENCE: 73
ccaacgacgc agagaaacac aag                                           23

<210> SEQ ID NO 74
<211> LENGTH: 23
<212> TYPE: DNA
<213> ORGANISM: Artificial
<220> FEATURE:
<223> OTHER INFORMATION: Synthetic oligonucleotide

<400> SEQUENCE: 74
cttgtgtttc tctgcgtcgt tgg                                           23

<210> SEQ ID NO 75
<211> LENGTH: 23
<212> TYPE: DNA
<213> ORGANISM: Artificial
<220> FEATURE:
<223> OTHER INFORMATION: Synthetic oligonucleotide

<400> SEQUENCE: 75
ccaacgacgc agagaaacac aag                                           23

<210> SEQ ID NO 76
<211> LENGTH: 23
<212> TYPE: RNA
<213> ORGANISM: Artificial
<220> FEATURE:
<223> OTHER INFORMATION: Synthetic oligonucleotide

<400> SEQUENCE: 76
cuuguguuuc ucugcgucgu ugg                                           23

<210> SEQ ID NO 77
<211> LENGTH: 22
<212> TYPE: DNA
<213> ORGANISM: Artificial
<220> FEATURE:
<223> OTHER INFORMATION: Synthetic oligonucleotide

<400> SEQUENCE: 77
cttacagagg tgcctgcggt gc                                            22

<210> SEQ ID NO 78
<211> LENGTH: 22
<212> TYPE: DNA
<213> ORGANISM: Artificial
<220> FEATURE:
<223> OTHER INFORMATION: Synthetic oligonucleotide

<400> SEQUENCE: 78
```
gcaccgcagg cacctctgta ag    22

<210> SEQ ID NO 79
<211> LENGTH: 22
<212> TYPE: RNA
<213> ORGANISM: Artificial
<220> FEATURE:
<223> OTHER INFORMATION: Synthetic oligonucleotide

<400> SEQUENCE: 79
cuuacagagg ugccugcggu gc    22

<210> SEQ ID NO 80
<211> LENGTH: 22
<212> TYPE: RNA
<213> ORGANISM: Artificial
<220> FEATURE:
<223> OTHER INFORMATION: Synthetic oligonucleotide

<400> SEQUENCE: 80
gcaccgcagg caccucugua ag    22

<210> SEQ ID NO 81
<211> LENGTH: 22
<212> TYPE: DNA
<213> ORGANISM: Artificial
<220> FEATURE:
<223> OTHER INFORMATION: Synthetic oligonucleotide

<400> SEQUENCE: 81
gaacttacag aggtgcctgc gg    22

<210> SEQ ID NO 82
<211> LENGTH: 22
<212> TYPE: DNA
<213> ORGANISM: Artificial
<220> FEATURE:
<223> OTHER INFORMATION: Synthetic oligonucleotide

<400> SEQUENCE: 82
ccgcaggcac ctctgtaagt tc    22

<210> SEQ ID NO 83
<211> LENGTH: 22
<212> TYPE: RNA
<213> ORGANISM: Artificial
<220> FEATURE:
<223> OTHER INFORMATION: Synthetic oligonucleotide

<400> SEQUENCE: 83
gaacuuacag aggugccugc gg    22

<210> SEQ ID NO 84
<211> LENGTH: 22
<212> TYPE: RNA
<213> ORGANISM: Artificial
<220> FEATURE:
<223> OTHER INFORMATION: Synthetic oligonucleotide

<400> SEQUENCE: 84
ccgcaggcac cucuguaagu uc    22

<210> SEQ ID NO 85
<211> LENGTH: 21
<212> TYPE: DNA
<213> ORGANISM: Artificial

```
<220> FEATURE:
<223> OTHER INFORMATION: Synthetic oligonucleotide

<400> SEQUENCE: 85
caggacacag tggcttttga c                                             21

<210> SEQ ID NO 86
<211> LENGTH: 21
<212> TYPE: DNA
<213> ORGANISM: Artificial
<220> FEATURE:
<223> OTHER INFORMATION: Synthetic oligonucleotide

<400> SEQUENCE: 86
gtcaaaagcc actgtgtcct g                                             21

<210> SEQ ID NO 87
<211> LENGTH: 21
<212> TYPE: RNA
<213> ORGANISM: Artificial
<220> FEATURE:
<223> OTHER INFORMATION: Synthetic oligonucleotide

<400> SEQUENCE: 87
caggacacag uggcuuuuga c                                             21

<210> SEQ ID NO 88
<211> LENGTH: 21
<212> TYPE: RNA
<213> ORGANISM: Artificial
<220> FEATURE:
<223> OTHER INFORMATION: Synthetic oligonucleotide

<400> SEQUENCE: 88
gucaaaagcc acuguguccu g                                             21

<210> SEQ ID NO 89
<211> LENGTH: 23
<212> TYPE: DNA
<213> ORGANISM: Artificial
<220> FEATURE:
<223> OTHER INFORMATION: Synthetic oligonucleotide

<400> SEQUENCE: 89 gcttttgtc cagatgtctt tgc                                            23

<210> SEQ ID NO 90
<211> LENGTH: 23
<212> TYPE: DNA
<213> ORGANISM: Artificial
<220> FEATURE:
<223> OTHER INFORMATION: Synthetic oligonucleotide

<400> SEQUENCE: 90
gcaaagacat ctggacaaaa agc                                           23

<210> SEQ ID NO 91
<211> LENGTH: 23
<212> TYPE: RNA
<213> ORGANISM: Artificial
<220> FEATURE:
<223> OTHER INFORMATION: Synthetic oligonucleotide

<400> SEQUENCE: 91 gcuuuuguc cagaugucuu ugc                                            23
```

```
<210> SEQ ID NO 92
<211> LENGTH: 23
<212> TYPE: RNA
<213> ORGANISM: Artificial
<220> FEATURE:
<223> OTHER INFORMATION: Synthetic oligonucleotide

<400> SEQUENCE: 92
gcaaagacau cuggacaaaa agc                                            23

<210> SEQ ID NO 93
<211> LENGTH: 23
<212> TYPE: DNA
<213> ORGANISM: Artificial
<220> FEATURE:
<223> OTHER INFORMATION: Synthetic oligonucleotide

<400> SEQUENCE: 93
gcaatgtagg tgtatctcca tgc                                            23

<210> SEQ ID NO 94
<211> LENGTH: 23
<212> TYPE: DNA
<213> ORGANISM: Artificial
<220> FEATURE:
<223> OTHER INFORMATION: Synthetic oligonucleotide

<400> SEQUENCE: 94
gcatggagat acacctacac cgc                                            23

<210> SEQ ID NO 95
<211> LENGTH: 23
<212> TYPE: RNA
<213> ORGANISM: Artificial
<220> FEATURE:
<223> OTHER INFORMATION: Synthetic oligonucleotide

<400> SEQUENCE: 95
gcaauguagg uguaucucca ugc                                            23

<210> SEQ ID NO 96
<211> LENGTH: 23
<212> TYPE: RNA
<213> ORGANISM: Artificial
<220> FEATURE:
<223> OTHER INFORMATION: Synthetic oligonucleotide

<400> SEQUENCE: 96
gcauggagau acaccuacac cgc                                            23

<210> SEQ ID NO 97
<211> LENGTH: 27
<212> TYPE: DNA
<213> ORGANISM: Artificial
<220> FEATURE:
<223> OTHER INFORMATION: Synthetic oligonucleotide

<400> SEQUENCE: 97
aatttaatac gactcactat agggaga                                        27

<210> SEQ ID NO 98
<211> LENGTH: 27
<212> TYPE: DNA
<213> ORGANISM: Artificial
<220> FEATURE:
<223> OTHER INFORMATION: Synthetic oligonucleotide
```

```
<400> SEQUENCE: 98
tctccctata gtgagtcgta ttaaatt                                            27

<210> SEQ ID NO 99
<211> LENGTH: 27
<212> TYPE: RNA
<213> ORGANISM: Artificial
<220> FEATURE:
<223> OTHER INFORMATION: Synthetic oligonucleotide

<400> SEQUENCE: 99
aauuuaauac gacucacuau agggaga                                            27

<210> SEQ ID NO 100
<211> LENGTH: 27
<212> TYPE: RNA
<213> ORGANISM: Artificial
<220> FEATURE:
<223> OTHER INFORMATION: Synthetic oligonucleotide

<400> SEQUENCE: 100
ucucccuaua gugagucgua uuaaauu                                            27

<210> SEQ ID NO 101
<211> LENGTH: 40
<212> TYPE: DNA
<213> ORGANISM: Artificial
<220> FEATURE:
<223> OTHER INFORMATION: Synthetic oligonucleotide

<400> SEQUENCE: 101
tcgtttttca ttaaggtgtc taagttttc tgctggattc                               40

<210> SEQ ID NO 102
<211> LENGTH: 40
<212> TYPE: DNA
<213> ORGANISM: Artificial
<220> FEATURE:
<223> OTHER INFORMATION: Synthetic oligonucleotide

<400> SEQUENCE: 102
gaatccagca gaaaaactta gacaccttaa tgaaaaacga                              40

<210> SEQ ID NO 103
<211> LENGTH: 40
<212> TYPE: RNA
<213> ORGANISM: Artificial
<220> FEATURE:
<223> OTHER INFORMATION: Synthetic oligonucleotide

<400> SEQUENCE: 103 ucguuuuca uuaagguguc uaaguuuuc ugcuggauuc                                40

<210> SEQ ID NO 104
<211> LENGTH: 40
<212> TYPE: RNA
<213> ORGANISM: Artificial
<220> FEATURE:
<223> OTHER INFORMATION: Synthetic oligonucleotide

<400> SEQUENCE: 104
gaauccagca gaaaaacuua gacaccuuaa ugaaaaacga                              40

<210> SEQ ID NO 105
```

```
<210> SEQ ID NO 105
<211> LENGTH: 23
<212> TYPE: DNA
<213> ORGANISM: Artificial
<220> FEATURE:
<223> OTHER INFORMATION: Synthetic oligonucleotide

<400> SEQUENCE: 105
gcaatgttgc cttaggtcca tgc                                              23

<210> SEQ ID NO 106
<211> LENGTH: 23
<212> TYPE: DNA
<213> ORGANISM: Artificial
<220> FEATURE:
<223> OTHER INFORMATION: Synthetic oligonucleotide

<400> SEQUENCE: 106
gcatggacct aaggcaacat tgc                                              23

<210> SEQ ID NO 107
<211> LENGTH: 23
<212> TYPE: RNA
<213> ORGANISM: Artificial
<220> FEATURE:
<223> OTHER INFORMATION: Synthetic oligonucleotide

<400> SEQUENCE: 107
gcaauguugc cuuaggucca ugc                                              23

<210> SEQ ID NO 108
<211> LENGTH: 23
<212> TYPE: RNA
<213> ORGANISM: Artificial
<220> FEATURE:
<223> OTHER INFORMATION: Synthetic oligonucleotide

<400> SEQUENCE: 108
gcauggaccu aaggcaacau ugc                                              23

<210> SEQ ID NO 109
<211> LENGTH: 22
<212> TYPE: DNA
<213> ORGANISM: Artificial
<220> FEATURE:
<223> OTHER INFORMATION: Synthetic oligonucleotide

<400> SEQUENCE: 109
cggtttctgg caccgcaggc ac                                               22

<210> SEQ ID NO 110
<211> LENGTH: 22
<212> TYPE: DNA
<213> ORGANISM: Artificial
<220> FEATURE:
<223> OTHER INFORMATION: Synthetic oligonucleotide

<400> SEQUENCE: 110
gtgcctgcgg tgccagaaac cg                                               22

<210> SEQ ID NO 111
<211> LENGTH: 22
<212> TYPE: RNA
<213> ORGANISM: Artificial
<220> FEATURE:
<223> OTHER INFORMATION: Synthetic oligonucleotide

<400> SEQUENCE: 111
```
cgguuucugg caccgcaggc ac                                              22

<210> SEQ ID NO 112
<211> LENGTH: 22
<212> TYPE: RNA
<213> ORGANISM: Artificial
<220> FEATURE:
<223> OTHER INFORMATION: Synthetic oligonucleotide

<400> SEQUENCE: 112
gugccugcgg ugccagaaac cg                                              22

<210> SEQ ID NO 113
<211> LENGTH: 23
<212> TYPE: DNA
<213> ORGANISM: Artificial
<220> FEATURE:
<223> OTHER INFORMATION: Synthetic oligonucleotide

<400> SEQUENCE: 113
gcaatgtagc cgtatgtcca tgc                                             23

<210> SEQ ID NO 114
<211> LENGTH: 23
<212> TYPE: DNA
<213> ORGANISM: Artificial
<220> FEATURE:
<223> OTHER INFORMATION: Synthetic oligonucleotide

<400> SEQUENCE: 114
gcatggacat acggctacat tgc                                             23

<210> SEQ ID NO 115
<211> LENGTH: 23
<212> TYPE: RNA
<213> ORGANISM: Artificial
<220> FEATURE:
<223> OTHER INFORMATION: Synthetic oligonucleotide

<400> SEQUENCE: 115
gcaauguagc cguaugucca ugc                                             23

<210> SEQ ID NO 116
<211> LENGTH: 23
<212> TYPE: RNA
<213> ORGANISM: Artificial
<220> FEATURE:
<223> OTHER INFORMATION: Synthetic oligonucleotide

<400> SEQUENCE: 116
gcauggacau acggcuacau ugc                                             23

<210> SEQ ID NO 117
<211> LENGTH: 38
<212> TYPE: DNA
<213> ORGANISM: Artificial
<220> FEATURE:
<223> OTHER INFORMATION: Synthetic oligonucleotide

<400> SEQUENCE: 117
cacttcactg caagacatag aaataacctg tgtatatt                              38

<210> SEQ ID NO 118
<211> LENGTH: 38
<212> TYPE: DNA

<213> ORGANISM: Artificial
<220> FEATURE:
<223> OTHER INFORMATION: Synthetic oligonucleotide

<400> SEQUENCE: 118
aatatacaca ggttatttct atgtcttgca gtgaagtg             38

<210> SEQ ID NO 119
<211> LENGTH: 38
<212> TYPE: RNA
<213> ORGANISM: Artificial
<220> FEATURE:
<223> OTHER INFORMATION: Synthetic oligonucleotide

<400> SEQUENCE: 119
cacuucacug caagacauag aaauaaccug uguauauu             38

<210> SEQ ID NO 120
<211> LENGTH: 38
<212> TYPE: RNA
<213> ORGANISM: Artificial
<220> FEATURE:
<223> OTHER INFORMATION: Synthetic oligonucleotide

<400> SEQUENCE: 120
aauauacaca gguuauuucu augucuugca gugaagug             38

<210> SEQ ID NO 121
<211> LENGTH: 32
<212> TYPE: DNA
<213> ORGANISM: Artificial
<220> FEATURE:
<223> OTHER INFORMATION: Synthetic oligonucleotide

<400> SEQUENCE: 121
ttattaataa ggtgcctgcg gtgccagaaa cc             32

<210> SEQ ID NO 122
<211> LENGTH: 32
<212> TYPE: DNA
<213> ORGANISM: Artificial
<220> FEATURE:
<223> OTHER INFORMATION: Synthetic oligonucleotide

<400> SEQUENCE: 122
ggtttctggc accgcaggca ccttattaat aa             32

<210> SEQ ID NO 123
<211> LENGTH: 32
<212> TYPE: RNA
<213> ORGANISM: Artificial
<220> FEATURE:
<223> OTHER INFORMATION: Synthetic oligonucleotide

<400> SEQUENCE: 123
uuauuaauaa ggugccugcg gugccagaaa cc             32

<210> SEQ ID NO 124
<211> LENGTH: 32
<212> TYPE: RNA
<213> ORGANISM: Artificial
<220> FEATURE:
<223> OTHER INFORMATION: Synthetic oligonucleotide

<400> SEQUENCE: 124
gguuucuggc accgcaggca ccuuauuaau aa             32

```
<210> SEQ ID NO 125
<211> LENGTH: 23
<212> TYPE: DNA
<213> ORGANISM: Artificial
<220> FEATURE:
<223> OTHER INFORMATION: Synthetic oligonucleotide

<400> SEQUENCE: 125
gactctgtgt atggagacac att                                              23

<210> SEQ ID NO 126
<211> LENGTH: 23
<212> TYPE: DNA
<213> ORGANISM: Artificial
<220> FEATURE:
<223> OTHER INFORMATION: Synthetic oligonucleotide

<400> SEQUENCE: 126
aatgtgtctc catacacaga gtc                                              23

<210> SEQ ID NO 127
<211> LENGTH: 23
<212> TYPE: RNA
<213> ORGANISM: Artificial
<220> FEATURE:
<223> OTHER INFORMATION: Synthetic oligonucleotide

<400> SEQUENCE: 127
gacucugugu auggagacac auu                                              23

<210> SEQ ID NO 128
<211> LENGTH: 23
<212> TYPE: RNA
<213> ORGANISM: Artificial
<220> FEATURE:
<223> OTHER INFORMATION: Synthetic oligonucleotide

<400> SEQUENCE: 128
aaugugucuc cauacacaga guc                                              23
```